United States Patent [19]

Yamaguchi et al.

[11] Patent Number: 5,709,816
[45] Date of Patent: Jan. 20, 1998

[54] SINGLET OXYGEN QUENCHERS AND EXTERNAL COMPOSITIONS CONTAINING THE SAME

[75] Inventors: Masakazu Yamaguchi; Hiroyuki Ohsu; Eiichi Nishizawa; Mitsuru Sugiyama, all of Ichikai-machi; Koichi Nakamura, Tokyo; Yoshinori Takema, Ichikai-machi, all of Japan

[73] Assignee: Kao Corporation, Tokyo, Japan

[21] Appl. No.: 685,926

[22] Filed: Jul. 22, 1996

[30] Foreign Application Priority Data

| Jul. 21, 1899 | [JP] | Japan | 7-185792 |
| Jul. 21, 1995 | [JP] | Japan | 7-185793 |
| Dec. 25, 1995 | [JP] | Japan | 7-336840 |
| Dec. 25, 1995 | [JP] | Japan | 7-336841 |
| Dec. 25, 1995 | [JP] | Japan | 7-336842 |
| Dec. 25, 1995 | [JP] | Japan | 7-336843 |

[51] Int. Cl.⁶ .................... A61K 7/50; C07C 211/00
[52] U.S. Cl. .................... 252/188.28; 514/646; 564/443
[58] Field of Search .................... 564/443; 574/646; 252/188.28

[56] References Cited

PUBLICATIONS

Vartanyan et al. CA No. 215414, vol. 92, 1980.
Earle et al. CA No. 231102, vol. 113, 1990.
Whetsel et al., Anal.Chem., 32, 730, 1960.
Smirnowa Zh. Vses.Khim.O'va im.D.I.Mendeleeva, 8, 235-236, 1963.
Malinowskii Zh.Obshch.Khim., 27, 1591, 1957.
Kuroki et al. Kogyo Kagaku, Zasshi, 59, 626-628, 1956.

*Primary Examiner*—Alan L. Rotman
*Assistant Examiner*—Lyman H. Smith
*Attorney, Agent, or Firm*—Oblon, Spivak, McClelland, Maier & Neustadt, Inc.

[57] ABSTRACT

Singlet oxygen quenchers containing as an active component a compound represented by the following formula or (2):

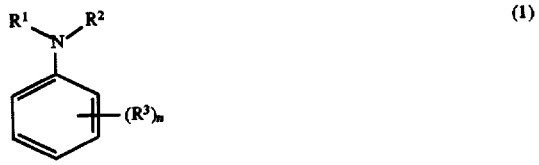

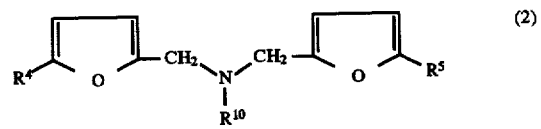

wherein each of $R^1$, $R^2$, $R^3$, $R^4$, $R^5$, $R^{10}$ and n are as described herein, and external compositions containing these compounds are provided for the prevention and treatment of various forms of damage to living bodies caused by singlet oxygen, and are thus quite useful as antiinflammation agents, anti-aging agents, agents preventing darkening of the skin, agents preventing protein denaturation, inhibitors against formation of sunburn cells, agents preventing lipid peroxidation, agents preventing DNA damage, and particularly in the fields of medicines and cosmetics as external compositions for the skin.

5 Claims, No Drawings

SINGLET OXYGEN QUENCHERS AND EXTERNAL COMPOSITIONS CONTAINING THE SAME

BACKGROUND OF THE INVENTION

1. Field of the Invention

The present invention relates to singlet oxygen quenchers and to external compositions having the ability to quench singlet oxygen generated in the skin and useful as cosmetics and drugs for the prevention of the effects of aging of the skin and to protect the hair from being damaged.

2. Description of the Related Art

It is widely known that different types of active oxygen are produced in the living body to cause a variety of undesirable effects. Examples of such active oxygen include singlet oxygen, hydroxyl radical, superoxide, and peroxides. Resulting byproducts of reactions between any of these and biological substances, such as unsaturated lipids, are also considered, in a broad sense, to fall in the category of active oxygen.

Recently, it has been determined that these active oxygens are related to many skin diseases, as well as to aging of the skin (Fragrance Journal, Vol 11, pp. 12–17 (1993)). Thus, external compositions having various active oxygen quenching activities have been proposed. However, most of these are extracts of animal or vegetable origin, and therefore, their use as external compositions is restricted because of the risk of causing allergic reactions.

Singlet oxygen is the most reactive among the types of active oxygen, and tends to cause inflammation, darkening of the skin, aging, protein denaturation, formation of sunburn cells, peroxidation of lipids, and DNA damage. Therefore, attempts have been made to exploit singlet oxygen quenchers as external compositions (Japanese Patent Application Laid-Open (Kokai) Nos. 5-320036, 6-329530, and 7-233046).

However, the action of previously disclosed singlet oxygen quenchers is not satisfactory, and in addition, many of them are problematic in their use as external compositions due to toxicity, causing allergic reactions and insufficient chemical stability of the quenchers themselves.

Therefore, singlet oxygen quenchers having an excellent ability to quench singlet oxygen and which are easily applied to the skin, with good compatibility are still desired, as are external compositions comprising such singlet oxygen quenchers.

SUMMARY OF THE INVENTION

Accordingly, one object of the present invention is to provide singlet oxygen quenchers having high singlet oxygen quenching capability and compatible with both the skin and hair.

A further object of the present invention is to provide compositions for use on the skin and/or hair that incorporate these singlet oxygen quenchers.

A further object of the present invention is to provide a method for the treatment and prevention of the effects of singlet oxygen on the skin and hair by the application of compositions containing the present singlet oxygen quenchers.

These and other objects of the present invention have been satisfied by the discovery of singlet oxygen quenchers comprising aniline derivatives and difurfuryl amine derivatives, particularly N,N-di-substituted aniline, that exhibit excellent singlet oxygen removal properties, and that prevent various reactions caused by singlet oxygen on the skin or hair including inflammation, aging, darkening of the skin, protein denaturation, formation of sunburn cells; peroxidation of lipids, DNA damage, and damage to the hair.

DETAILED DESCRIPTION OF THE PREFERRED EMBODIMENTS

The present invention provides a singlet oxygen quencher comprising, as an active component, an N,N-disubstituted aniline derivative represented by the following formula (1) or a salt thereof:

wherein each of $R^1$ and $R^2$, independently, represents an alkyl group which may be substituted by 1–3 groups selected from the group consisting of a hydroxyl group, alkoxyl groups, and hydroxyalkoxyl groups; an arylmethyl group which may be substituted by 1–3 groups selected from the group consisting of a hydroxyl group, alkoxyl groups, hydroxyalkoxyl groups, alkyl groups, and hydroxyalkyl groups; a heteroarylmethyl group which may be substituted by 1–3 groups selected from the group consisting of a hydroxyl group, alkoxyl groups, hydroxyalkoxyl groups, alkyl groups, and hydroxyalkyl groups; each of $R^3$s in the number of n, which are substituents on the benzene ring, independently represents a hydrogen atom, a hydroxyl group, an alkoxyl group, a hydroxyalkoxyl group, an alkyl group, a hydroxyalkyl group, or a hydroxyalkoxyalkyl group; and n represents an integer between 1 and 4 inclusive; provided that cases where $R^1$ and $R^2$ are both nonsubstituted alkyl groups are excluded.

The present invention also provides an external composition comprising the N,N-di-substituted aniline derivative represented by the above formula (1) or a salt thereof in a dermatologioally acceptable carrier. (The term "dermatologically acceptable" as used herein means compatible with either or both of the skin and hair.)

A further embodiment of the present invention provides a singlet oxygen quencher comprising, as an active component, a compound represented by the following formula (2) or a salt thereof:

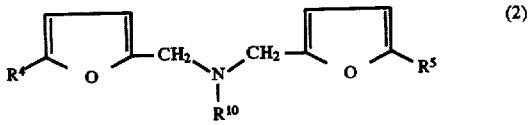

wherein each of $R^4$ and $R^5$, independently, represents a hydrogen atom or an alkyl group which may be substituted by a hydroxyl group; and $R^{10}$ represents an alkyl group which may be substituted by 1 or 2 groups selected from the group consisting of a hydroxyl group, alkoxyl groups, hydroxyalkoxyl groups, and alkoxycarbonyl groups.

The present invention also provides an external composition comprising the compound represented by the above formula (2) or a salt thereof in a dermatologically acceptable carrier.

In a further embodiment, the present invention provides a compound represented by the following formula (1a) or a salt thereof:

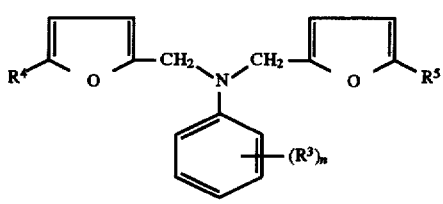

(1a)

wherein $R^3$, $R^4$, $R^5$, and n have the same meanings as defined above.

The present invention also provides a compound represented by the following formula (1b) or a salt thereof:

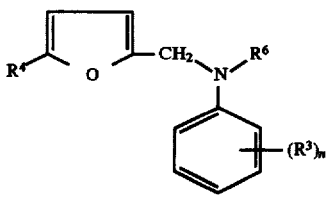

(1b)

wherein $R^6$ represents an alkyl group which may be substituted by 1 or 2 groups selected from the group consisting of hydroxy groups and alkoxy groups; $R^3$, $R^4$, and n have the same meanings as defined above; with the following cases (1) and (2) being excluded: (1) $R^4$ is a hydrogen atom, $R^6$ is a methyl group, and $R^3$ is a hydrogen atom, a methyl group substituted at the 2-position on the benzene ring, a methyl group substituted at the 4-position on the benzene ring, or a methoxyl group substituted at the 4-position on the benzene ring; (2) $R^4$ is a hydrogen atom, $R^6$ is an ethyl group, and $R^3$ is a methyl group substituted at the 4-position on the benzene ring, or a methoxyl group substituted at the 4-position on the benzene ring.

The present invention also provides a compound represented by the following formula (1c) or a salt thereof:

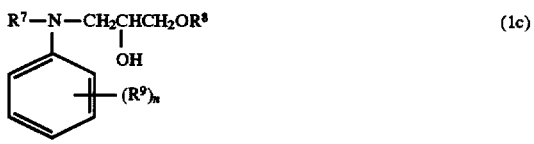

(1c)

wherein $R^7$ represents an alkyl group, $R^8$ represents a hydrogen atom or an alkyl group; each of $R^9$s in the number of n, which are substituents on the benzene ring, independently represents a hydrogen atom, an alkyl group, or an alkoxyl group; and n represents an integer between 1 and 4 inclusive; with the following cases (1) through (4) being excluded: (1) $R^8$ and $R^9$s in the number of n are all hydrogen atoms; (2) $R^8$ is a hydrogen atom, $R^7$ is an ethyl group, n is 1, and $R^9$ is a methyl group substituted at the meta-position; (3) $R^7$ and $R^8$ are both methyl groups and $R^9$s in the number of n are all hydrogen atoms; (4) $R^7$ and $R^8$ are both methyl groups, n is 1, and $R^9$ is a methyl group substituted at the meta-position.

The external compositions of the present invention effectively prevent various forms of damage to living bodies caused by singlet oxygen, and thus are quite useful as antiinflammation agents, anti-aging agents, agents preventing darkening of the skin, agents preventing protein denaturation, inhibitors against formation of sunburn cells, agents preventing lipid peroxidation, agents preventing DNA damage, and, particularly in the fields of medicines and cosmetics, as external compositions for the skin.

In the present invention, alkyl groups preferably have 1 to 12 carbon atoms. C1–C2 linear or branched alkyl groups are more preferred. Specific examples of suitable alkyl groups include methyl, ethyl, propyl, isopropyl, butyl, isobutyl, sec-butyl, tert-butyl, 2-methylbutyl, n-pentyl, isopentyl, neopentyl, n-hexyl, n-heptyl, n-octyl, 2-ethylhexyl, n-nonyl, isononyl, n-decyl, n-undecyl, and n-dodecyl.

The alkoxyl groups of the present invention preferably have 1 to 10 carbon atoms. C1–C10 linear or branched alkoxyl groups are more preferred, and C1–C8 linear or branched alkoxyl groups are most preferred. Specific examples of suitable alkoxyl groups include methoxyl, ethoxyl, n-propoxyl, isopropoxyl, n-butoxyl, sec-butoxyl, tert-butoxyl, and 2-ethylhexyloxyl.

Hydroxyalkyl groups of the present invention preferably have from 1 to 12 carbon atoms. C1–C12 linear or branched hydroxyalkyl groups are more preferred, and C1–C8 hydroxyalkyl groups are still more preferred. Particularly preferred are C1–C4 hydroxyalkyl groups. Specific examples of suitable hydroxyalkyl groups include 2-hydroxyethyl, 2-hydroxypropyl, 3-hydroxypropyl, 2-hydroxybutyl, 3-hydroxybutyl, and 4-hydroxybutyl.

Hydroxyalkoxyl groups of the present compounds preferably have from 1 to 10 carbon atoms. C1–C10 linear or branched hydroxyalkoxyl groups are more preferred, and C1–C8 hydroxyalkoxyl groups are still more preferred. Particularly preferred are C1–C4 hydroxyalkoxyl groups. Specific examples of suitable hydroxyalkoxyl groups include hydroxymethoxyl, 2-hydroxyethoxyl, and 3-hydroxypropoxyl.

The alkoxycarbonyl groups of the present invention preferably have a total of from 2 to 11 carbon atoms (including the carbonyl carbon). C2–C9 alkoxycarbonyl groups are more preferred, and C2–C5 alkoxycarbonyl groups are still more preferred. Specific examples of suitable alkoxycarbonyl groups include methoxycarbonyl and ethoxycarbonyl.

Hydroxyalkoxyalkyl groups of the present invention are preferably hydroxy C1–C10 alkoxy C1–C12 alkyl groups, more preferably hydroxy C1–C4 alkoxy C1–C8 alkyl groups, and most preferably hydroxy C1–C4 alkoxy C1–C4 alkyl groups. Specific examples of suitable hydroxyalkoxyalkyl groups include 2-hydroxyethoxyethyl and 2-hydroxyethoxypropyl.

Suitable examples of arylmethyl groups include benzyl groups and naphthylmethyl groups, with benzyl groups being preferred. Suitable examples of heteroaryl methyl groups include furfuryl groups, benzofuranyl methyl groups, pyridyl methyl groups, pyrrole methyl groups, oxazolyl methyl groups, thiazolyl methyl groups, pyridazinyl methyl groups, pyrimidinyl methyl groups, indolyl methyl groups, quinolinyl methyl groups, and isoquinolinyl methyl groups. Of these, furfuryl groups and benzofuranyl methyl groups are more preferred with furfuryl groups being most preferred.

In the present invention, alkyl groups, arylmethyl groups, and heteroarylmethyl groups may optionally have from 1 to 3 of the previously described substitutents. Specific examples of alkyl groups having alkoxyl groups as substituents include 2-methoxyethyl, 3-methoxypropyl, and 4-methoxybutyl. Examples of alkyl groups each having 2 hydroxyl groups as substituents include 2,3-dihydroxypropyl. Examples of alkyl groups each having 2 alkoxyl groups as substituents include 2,3-dimethoxypropyl. Examples of alkyl groups having hydroxyl groups and alkoxyl groups as substituents include 2-hydroxy-3-methoxypropyl and 2-hydroxy-3-(2-ethylhexyloxy)propyl. Examples of alkyl groups having hydroxyalkoxyl groups as substituents include the aforementioned hydroxyalkoxyalkyl groups. Examples of alkyl groups having hydroxy groups and hydroxyalkoxyl groups as substituents include 2-hydroxy-3-(hydroxyethoxy)propyl. Examples of particularly preferred substituted arylmethyl groups and substituted heteroarylmethyl groups include p-hydroxybenzyl, p-methoxybenzyl, 5-hydroxymethylfurfuryl, and 5-methylfurfuryl.

Although from 1 to 4 R³ groups may be optionally substituted on a benzene ring, the number of R³ groups which may be substituted on a benzene ring is preferably from 1 to 3, and more preferably 1 or 2. R³'s are preferably hydrogen atoms, methoxy groups, or 2–3 differing groups selected from methoxy, methyl, and hydroxyethyl.

Salts of N,N-di-substituted aniline derivatives of formula (1) and salts of compounds of formula (2) are not particularly limited so long as they are pharmaceutically acceptable. Suitable salts include salts of mineral acids, such as hydrochlorides and sulfates; and salts of organic acids, such as acetates, succinates, and oxalates. The compounds of the present invention may also be present as hydrates.

The N,N-di-substituted aniline derivatives of formula (1) can be prepared using various conventional methods. For example, the derivatives may be prepared in accordance with, but are not limited to, either of the following methods (A) or (B).

Method (A):

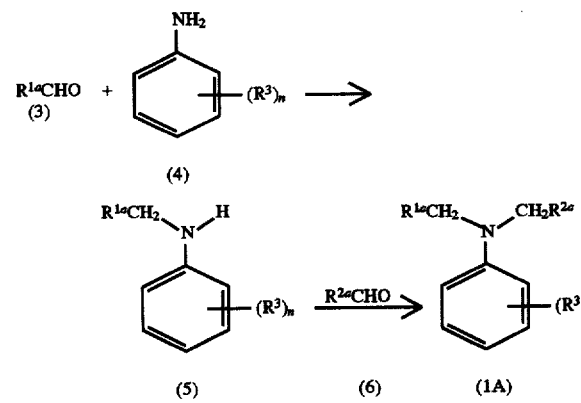

wherein $R^{1a}$ represents a group satisfying $R^{1a}CH_2=R^1$, $R^{2a}$ represents a group satisfying $R^{2a}CH_2=R^2$, and $R^3$ and n have the same meanings as defined before.

Briefly, an aldehyde (3) is reacted with an aniline (4) under reducing conditions, and the resultant compound (5 is reacted with an aldehyde (6) under reducing conditions, to provide compound (1A).

The reaction involving aldehyde (3) and aniline (4) and that involving compound (5) and aldehyde (6) may both be performed by heating between 0° and 200° C. in an alcohol solvent, such as methanol and ethanol, in the presence of either a borane compound, such as a borane-pyridine complex (A. E. Moormann, Synth. Commun., 1993, 23, 789), or a sodium cyanoborohydride (R. F. Borch et al., J. Am. Chem. Soc., 1971, 93, 2879).

Method (B):

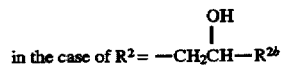

Method (B):

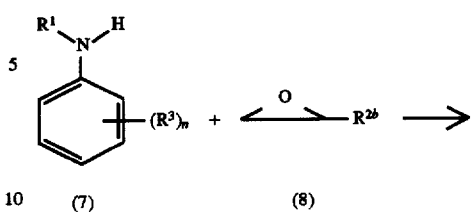

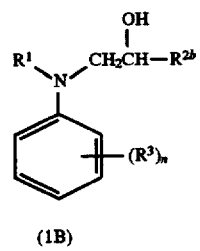

wherein $R^{2b}$ represents a group satisfying $R^{2b}CH_2(OH)$ $CH_2=R^2$ and $R^1$, $R^3$, and n have the same meanings as defined before.

Briefly, when a compound (7) is reacted with an epoxy compound (8), an N,N-di-substituted aniline derivative (1B) having a 2-hydroxyethyl group can be obtained.

This reaction may be performed using a compound (5) obtained in the above-mentioned reaction (A) and a compound (8) in the absence of a solvent or in an alcohol solvent such as methanol and ethanol while heating the system within a temperature range between 20° and 200° C.

The present compounds represented by formula (2) may be prepared in a manner similar to that described in the above synthesis methods, using an amine ($R^{10}NH_2$) in place of aniline (4). Also, in order to obtain a compound of formula (1) in which $R^1$ and $R^2$ are identical, the above method (A) may be modified to a one step reaction using at least twice the molar amount of aldehyde (3) than of compound (4).

The thus-obtained N,N-di-substituted aniline derivatives of formula (1), compounds of formula (2), or their salts possess excellent singlet oxygen removal properties. These compounds also prevent and/or treat a variety of abnormal conditions of the skin and hair that are attributed to singlet oxygen, including inflammation, aging (e.g., formation of wrinkles), darkening of the skin, protein denaturation, formation of sunburn cells, peroxidation of lipids, and DNA damage. Thus, the compounds can be advantageously used as ingredients of external compositions for the skin and hair.

The external compositions according to the present invention are manufactured by routine methods using an N,N-di-substituted aniline derivative of formula (1), a compound of formula (2), or a salt of any of these in combination with conventional dermatologically acceptable carriers including bases for external medicines, cosmetics, or hair-care products. Generally, the amounts of N,N-di-substituted aniline derivatives of formula (1), compounds of formula (2), or of their salts incorporated in such external compositions are between 0.001 and 20% by weight and preferably between 0.01 and 10% by weight based on the total weight of the composition.

Using routine methods, the external compositions of the present invention may be formulated into a variety of preparations, depending on the intended use. These preparations include, but are not limited to, external skin compositions for medical use, external skin cosmetic compositions, and hair cosmetic compositions. As external skin compositions for medical use and external skin cosmetic compositions, many types of ointments containing a medicinal component may be used. The ointments may contain either an oil base or an emulsion base, including oil-in-water type and water-in-oil type emulsions.

The oil base is not particularly limited with vegetable oils, animal oils, synthetic oils, fatty acids, and natural or synthetic glycerides being suitable. The medicinal component is also not particularly limited. For example, analgesic/anti-inflammatory agents, analgesics, bactericidal/disinfectant agents, astringents, skin softening agents, hormones, and vitamins may be used as needed.

When the external compositions of the present invention are used as cosmetic compositions, the following ingredients may be optionally incorporated in arbitrary combinations as desired and determined in accordance with conventional skill in the art: oils, humectants, whitening agents, UV absorbers, alcohols, chelating agents, pH modifiers, preservatives, viscosityincreasing agents, colorants, and perfumes which are ordinarily used as cosmetic components. Cosmetic compositions may have various uses and may take various shapes accordingly, such as oil-in-water type or water-in-oil type emulsions, creams, cosmetic milks, lotions, oily cosmetics, packs, foundations, lipsticks, etc.

Having generally described this invention, a further understanding can be obtained by reference to certain specific examples which are provided herein for purposes of illustration only and are not intended to be limiting unless otherwise specified.

EXAMPLES

Synthesis Example 1:

p-Anisidine (36.95 g) and methyl glycidyl ether (29.07 g) in methanol (50 ml) were placed in a 200-ml round-bottomed flask equipped with a magnetic stirrer and a reflux condenser, and the mixture was refluxed overnight. The solvent was distilled off and the resultant yellow oil was distilled under reduced pressure to obtain 33.75 g of a pale yellow intermediate (yield 53%).

Into a 200-ml two-necked flask equipped with a magnetic stirrer, a reflux condenser, and a 25-ml dropping funnel were placed the pale yellow intermediate obtained in the above step (12–68 g), 35% formalin solution (7.72 g), and acetic acid (3.60 g) in methanol (100 ml), and the mixture was then cooled on ice. Sodium cyanoborohydride (2.26 g) in methanol (10 ml) was added to the flask dropwise over approximately 10 minutes. After completion of addition, the mixture was stirred for 30 minutes with cooling on ice, and stirred for a further 4 hours at room temperature. The solvent was evaporated, and the resultant yellow oil was dissolved in ethyl acetate (100 ml). The resultant solution was successively washed using a 2N aqueous NaOH solution and brine, after which the solvent was evaporated to yield a yellow oil. The resultant yellow oil was purified by silica gel column chromatography (solvents: hexane 2+ethyl acetate 1) to obtain 11.18 g of a purified pale yellow product (yield: 83%).

Through analysis by $^1$H-NMR, the purified product was identified to be N-(2-hydroxy-3-methoxypropyl)-N-methyl-p-anisidine (compound (1)).

$^1$H-NMR (CDCl$_3$, δ): 2.70 (bs, 1H), 2.88 (s, 3H), 3.25 (d, 2H, J=6.6 Hz), 3.35–3.51 (m, 2H), 3.39 (s, 3H), 3.76 (s, 3H), 3.99–4.11 (m, 1H), 6.81 (s-like, 4H).

Synthesis Example 2:

The pale yellow intermediate (8.45 g) obtained in synthesis Example 1, n-butyraldehyde (4.33 g), and acetic acid (2.40 g), in methanol (100 ml), were placed in a 200-ml two-necked flask equipped with a magnetic stirrer, a reflux condenser, and a 25-ml dropping funnel. The flask was cooled on ice. Sodium cyanoborohydride (1.51 g) in methanol (10 ml) was added dropwise over approximately 10 minutes. After completion of addition, the mixture was stirred for 30 minutes with cooling on ice, and stirred for a further 4 hours at room temperature. The solvent was evaporated, and the resultant yellow oil was dissolved in ethyl acetate (100 ml). The resultant solution was successively washed using 2N aqueous NaOH solution and brine, after which the solvent was evaporated to yield a yellow oil. The yellow oil was purified by silica gel column chromatography (solvents: hexane 5+ethyl acetate 1) to obtain 8.17 g of a purified pale yellow product (yield: 76%).

Through analysis by $^1$H-NMR, the purified product was identified to be N-n-butyl-N-(2-hydroxy-3-methoxypropyl)-p-anisidine (compound (2)).

$^1$H-NMR (CDCl$_3$, δ): 0.91 (t, 3H, J=7.1 Hz), 1.22–1.57 (m, 4H), 2.72 (bs, 1H), 3.11–3.50 (m, 6H), 3.39 (s ,3H), 3.76 (s, 3H), 3.87–4.02 (m, 1H), 6.81 (s-like, 4H).

Synthesis Example 3:

The pale yellow intermediate (6.34 g) obtained in Synthesis Example 1, n-octyl aldehyde (5.77 g), and acetic acid (1.80 g), in methanol (100 ml), were placed in a 200-ml two-necked flask equipped with a magnetic stirrer, a reflux condenser, and a 25-ml dropping funnel. The flask was cooled on ice. Sodium cyanoborohydride (1.13 g) in methanol (10 ml) was added dropwise over approximately 10 minutes. After completion of addition, the mixture was stirred for 30 minutes with cooling on ice, and stirred for a further 4 hours at room temperature. The solvent was evaporated, and the resultant yellow oil was dissolved in ethyl acetate (100 ml). The resultant solution was successively washed using a 2N aqueous NaOH solution and brine, after which the solvent was evaporated to yield a yellow oil. The resultant yellow oil was purified by silica gel column chromatography (solvents: hexane 5+ethyl acetate 1) to obtain 8.50 g of a purified pale yellow product (yield: 88%).

Through analysis by $^1$H-NMR, the purified product was identified to be N-(2-hydroxy-3-methoxypropyl)-N-n-octyl-p-anisidine (compound (3)).

$^1$H-NMR (CDCl$_3$, δ) 0.88 (t, 3H, J=6.7 Hz), 1.10–1.60 (m, 12H), 2.68 (bs, 1H), 3.11–3.49 (m, 6H), 3.39 (s, 3H), 3.76 (s, 3H), 3.89–4.01 (m, 1H), 6.81 (s-like, 4H).

Synthesis Example 4:

(1) p-Toluidine (21.43 g) and methyl glycidyl ether (19.38 g) in methanol (50 ml) were placed in a 200-ml round-bottomed flask equipped with a magnetic stirrer and a reflux condenser, and the mixture was refluxed overnight. The solvent was distilled off and the resultant yellow oil was distilled under reduced pressure to obtain 20.04 g of a pale yellow intermediate (yield 51%) and 10.30 g of a pale yellow product (yield 18%).

Through analysis by $^1$H-NMR, the latter pale yellow product was identified as N,N-bis(2-hydroxy-3-methoxypropyl)-p-toluidine (compound (4)).

$^1$H-NMR (CDCl$_3$, δ): 2.25 (s, 3H), 3.16 (bs, 2H), 3.7–3.48 (m, 8H), 3.39 (s, 6H), 3.99–4.12 (m, 2H), 6.74 (d, 2H, J=8.4 Hz), 7.04 (d, 2H, J=8.4 Hz)

(2) Into a 200-ml two-necked flask equipped with a magnetic stirrer, a reflux condenser, and a 25-ml dropping funnel were placed the pale yellow intermediate obtained in the above step (9.76 g), n-butyraldehyde (5.41 g), and acetic acid (3.00 g) in methanol (100 ml), and the mixture was then cooled on ice. Sodium cyanoborohydride (1.89 g) in methanol (10 ml) was added to the flask dropwise over approximately 10 minutes. After completion of addition, the mixture was stirred for 30 minutes with cooling on ice, and stirred for a further 4 hours at room temperature. The solvent was evaporated, and the resultant yellow oil was dissolved in ethyl acetate (100 ml). The resultant solution was successively washed using a 2N aqueous NaOH solution and brine, after which the solvent was evaporated to yield a yellow oil. The yellow oil was purified by silica gel column chromatography (solvents: hexane 10+ethyl acetate 1) to obtain 10.67 g of a purified pale yellow product (yield: 85%).

Through analysis by $^1$H-NMR, the purified product was identified to be N-n-butyl-N-(2-hydroxy-3-methoxypropyl)-p-toluidine (compound (5)).

$^1$H-NMR (CDCl$_3$, δ): 0.92 (t, 3H, J=7.1 Hz), 1.23–1.61 (m, 4H), 2.24 (s, 3H), 2.51 (d, 1H, J=4.4 Hz), 3.21–3.51 (m, 6H), 3.39 (s, 3H), 3.93–4.07 (m, 1H), 6.69 (d, 2H, J=8.6 Hz), 7.03 (d, 2H, J=8.6 Hz).

Synthesis Example 5:

N-n-Butylaniline (7.46 g) and methyl glycidyl ether (6.61 g) in methanol (50 ml) were placed in a 200-ml round-bottomed flask equipped with a magnetic stirrer and a reflux condenser, and the mixture was refluxed overnight. The solvent was evaporated and the resultant yellow oil was purified by silica gel column chromatography (solvents: hexane 5+ethyl acetate 1) to obtain 10.60 g of a purified pale yellow product (yield: 89%).

Through analysis by $^1$H-NMR, the purified product was identified to be N-n-butyl-N-(2-hydroxy-3-methoxypropyl) aniline (compound (6)).

$^1$H-NMR (CDC$_3$, δ) 0.94 (t, 3H, J=7.2 Hz), 1.24–160 (m, 4H ), 2.45 (d, 1H, J=4.2 Hz), 3.26–3.52 (m, 6H), 3.40 (s, 3H), 3.97–4.10 (m, 1H), 6.66–6.86 (m, 3H), 7.16–7.35 (m, 2H),

Synthesis Example 6:

Into a 200-ml two-necked flask equipped with a magnetic stirrer, a reflux condenser, and a 25-ml dropping funnel were placed furfural (11.39 g), N-ethylaniline (12.15 g), and acetic acid (6.07 g) in methanol (100 ml), and the mixture was then cooled on ice. Sodium cyanoborohydride (2.52 g) in methanol (10 ml) was added to the flask dropwise over approximately 10 minutes. After completion of addition, the mixture was stirred for 30 minutes with cooling on ice, and refluxed for a further 2 hours. The flask was allowed to cool, and then the solvent was evaporated. The resultant yellow oil was dissolved in chloroform (100 ml). The resultant solution was successively washed using a 2N aqueous NaOH solution and brine, after which the solvent was evaporated to yield a yellow oil. The yellow oil was distilled under reduced pressure (bp.: 109°–114° C./1.0×10$^{-2}$ mmHg) to yield 16.00 g of a purified pale yellow product (yield: 79%).

Through analysis by $^1$H-NMR, the purified product was identified to be N-ethyl-N-phenyl-2-furanmethane amine (compound (7)).

$^1$H-NMR (CDCl$_3$, δ): 7.31 (dd, 1H, J=0.7, 1.8 Hz), 7.14–7.24 (m, 2H), 6.63–6.78 (m, 3H), 6.25 (dd, 1H, J=1.9, 3.2 Hz), 6.12 (dd, 1H, J=0.7, 3.2 Hz), 4.40 (s, 2H), 3.40 (q, 2H, J=7.1 Hz), 1.14 (t, 3H, J=7.1 Hz).

Synthesis Example 7:

Into a 500-ml two-necked flask equipped with a magnetic stirrer, a reflux condenser, and a 50-ml dropping funnel were placed 5-methylfurfural (22.02 g), N-ethylaniline (26.66 g), and acetic acid (13.21 g) in methanol (250 ml), and the mixture was then cooled on ice. Sodium cyanoborohydride (8.80 g) in methanol (25 ml) was added to the flask dropwise over approximately 10 minutes. After completion of addition, the mixture was stirred for 30 minutes with cooling on ice, and stirred for a further 15 hours at room temperature. The solvent was evaporated, and the resultant yellow oil was dissolved in chloroform (200 ml). The resultant solution was successively washed using a 2N aqueous NaOH solution and brine, after which the solvent was evaporated to yield a yellow oil. The resultant yellow oil was purified by bulb-to-bulb distillation under reduced pressure (bp.: 130° C./6.0×10$^{-3}$ mmHg) to give 25.48 g of a purified pale yellow product (yield: 59%).

Through analysis by $^1$H-NMR, the purified product was identified to be 5-methyl-N-ethyl-N-phenyl-2-furanmethane amine (compound (8)).

$^1$H-NMR (CDCl$_3$, δ): 7.10–7.30 (m, 2H, 6.10–6.30 (m, 3H), 6.01 (d, 1H, J=3.0 Hz), 5.85 (d, 1H, J=3.0 Hz), 4.37 (S, 2H), 3.43 (q, 2H, J=7.1 Hz) 2.26 (s, 3H), 1.16 (t, 3H, J=7.1 Hz)

Synthesis Example 8:

Into a 500-ml two-necked flask equipped with a magnetic stirrer, a reflux condenser, and a 50-ml dropping funnel were placed furfural (19.22 g), hydroxyethyl aniline (27.44 g), and acetic acid (12.01 g) in methanol (250 ml), and the mixture was then cooled on ice. Sodium cyanoborohydride (8.80 g) in methanol (25 ml) was added to the flask dropwise over approximately 10 minutes. After completion of addition, the mixture was stirred for 30 minutes with cooling on ice, and further refluxed overnight at 50° C. The flask was allowed to cool, and then the solvent was evaporated. The resultant yellow oil was dissolved in chloroform (200 ml). The resultant solution was successively washed using a 2N aqueous NaOH solution and brine, after which the solvent was evaporated to give a yellow oil. The resultant yellow oil was purified by silica gel column chromatography (solvents: hexane 4+ethyl acetate 1) to obtain 24.58 g of a purified pale yellow product (yield: 57%).

Through analysis by $^1$H-NMR, the purified product was identified to be N-hydroxyethyl-N-phenyl-2-furanmethane amine (compound (9)).

$^1$H-NMR (CDCl$_3$, δ): 7.34 (dd, 1H, J=0.6, 1.6 Hz), 7.20–7.30 (m, 2H), 6.70–6.90 (m, 3H), 6.30 (dd, 1H, J=1.6, 3.2 Hz), 6.17 (dd, 1H, J=0.6, 3.2 Hz), 4.51 (s, 2H), 3.79 (dt, 2H, J=5.6, 6.0 Hz), 3.57 (t 2H), J=5.6 Hz), 1.98 (t, 1H, J=6.0 Hz).

Synthesis Example 9:

Into a 100-ml two-necked flask equipped with a magnetic stirrer, a reflux condenser, and a 25-ml dropping funnel were placed 5-acetoxymethylfurfural (8.69 g), N-ethylaniline (6.32 g), and acetic acid (3.02 g) in methanol (50 ml), and the mixture was then cooled on ice. Sodium cyanoborohydride (1.27 g) in methanol (10 ml) was added to the flask dropwise over approximately 10 minutes. After completion of addition, the mixture was stirred for 30 minutes with cooling on ice, and stirred for a further 15 hours at room temperature. The solvent was evaporated, and the resultant yellow oil was dissolved in chloroform (200 ml). The resultant solution was successively washed using a 2N aqueous NaOH solution and brine, after which the solvent was evaporated to give a yellow oil. The resultant yellow oil was distilled under reduced pressure (bp.: 38°–140° C./8.9×10$^{-3}$ mmHg) to yield 6.28 g of a purified pale yellow product. The product was dissolved in methanol (20 ml) and powdery anhydrous potassium carbonate (2.78 g) was added. The resultant mixture was stirred for 1 hour at room temperature. A yellow oil obtained through removal of insoluble inorganic salts and evaporation of the solvent was purified by silica gel column chromatography (solvents: hexane 4+ethyl acetate 1) to obtain 4.30 g of a purified pale yellow product (yield: 36%).

Through analysis by $^1$H-NMR, the purified product was identified to be 5-hydroxymethyl-N-ethyl-N-phenyl-2-furanmethane amine (compound (10)).

$^1$H-NMR (CDCl$_3$, δ): 7.14–7.23 (m, 2H), 6.67–6.77 (m, 3H), 6.13 (d, 1H, J=3.1 Hz), 6.04 (d, 1H, J=3.1 Hz), 4.45 (s, 2H), 4.37 (s, 2H), 3.40 (q, 2H, J=7.1 Hz), 2.54 (bs, 1H), 1.14 (t, 3H, J=7.1 Hz).

Synthesis Example 10:

Into a 500-ml two-necked flask equipped with a magnetic stirrer, a reflux condenser, and a 100-ml dropping funnel were placed 5-methylfurfural (96.50 g), aniline (81.95 g), and acetic acid (52.84 g) in methanol (300 ml), and the mixture was then cooled on ice. Sodium cyanoborohydride (21.34 g) in methanol (50 ml) was added dropwise over approximately 20 minutes. After completion of addition, the mixture was stirred for 30 minutes with cooling on ice, and stirred for a further 4 hours at room temperature. The solvent was evaporated, and the resultant yellow oil was dissolved in chloroform (300 ml). The resultant solution was successively washed using a 2N aqueous NaOH solution and brine, after which the solvent was evaporated to give a yellow oil. The resultant yellow oil was distilled under reduced pressure (bp.: 104°–107° C./0.5 mmHg) to yield 146.0 g of a yellow oil (yield 89%).

Into a 300-ml round-bottomed flask equipped with a magnetic stirrer and a reflux condenser, were placed the yellow oil obtained in the above step (9.36 g) and 2-ethylhexanal (7.69 g) in ethanol (150 ml), and the mixture was then cooled on ice. A borane-pyridine complex (5.58 g) was added. The resultant mixture was stirred for 3 days at 80° C. The flask was allowed to cool, and then the solvent was evaporated. The resultant yellow oil was dissolved in ethyl acetate (200 ml). The solution was washed with brine, after which the solvent was evaporated to give a yellow oil. The resultant yellow oil was purified by silica gel column chromatography (solvents: hexane 4+ethyl acetate 1) to obtain 1.89 g of a purified pale yellow product (yield: 13%).

Through analysis by $^1$H-NMR, the purified product was identified to be 5-methyl-N-(2-ethylhexyl)-N-phenyl-2-furanmethane amine (compound (11)).

$^1$H-NMR (CDCl$_3$, δ): 7.10–7.30 (m, 2H), 6.60–6.80 (m, 3H), 5.94 (d, 2H, J=3.0 Hz), 5.84 (d, 2H, J=3.0 Hz), 4.40 (s, 2H) 3.23 (d, 2H, J=7.3 Hz), 2.25 (s, 3H), 1.20–1.80 (m, 9H), 0.80–1.00 (m, 6H).

Synthesis Example 11:

Into a 500-ml two-necked flask equipped with a magnetic stirrer, a reflux condenser, and a 50-ml dropping funnel were placed 5-methylfurfural (22.02 g), N-hydroxyethylaniline (30.18 g), and acetic acid (13.21 g) in methanol (250 ml), and the mixture was then cooled on ice. Sodium cyanoborohydride (8.80 g) in methanol (25 ml) was added to the flask dropwise over approximately 10 minutes. After completion of addition, the mixture was stirred for 30 minutes with cooling on ice, and further overnight at 50° C. The solvent was evaporated, and the resultant yellow oil was dissolved in chloroform (200 ml). The solution was successively washed using a 2N aqueous NaOH solution and brine, after which the solvent was evaporated to give a yellow oil. The resultant yellow oil was distilled under reduced pressure (bp.: 137°–139° C./7.1×10$^{-3}$ mmHg) to yield 21.22 g of a purified pale yellow product (yield 46%).

Through analysis by $^1$H-NMR, the purified product was identified to be 5-methyl-N-hydroxyethyl-N-phenyl-2-furanmethane amine (compound (12)).

$^1$H-NMR (CDCl$_3$, δ): 7.10–7.30 (m, 2H), 6.70–6.90 (m, 3H), 5.89 (d, 1H, J=3.0 Hz), 5.85 (d, 1H, J=3.0 Hz), 4.44 (s, 2H), 3.80 (dt, 2H, J=5.6, 6.1 Hz), 3.58 (t, 2H, J=5.6 Hz), 2.25 (s, 3H), 2.07 (t, 1H, J=6.1 Hz).

Synthesis is Example 12:

Into a 100-ml round-bottomed flask equipped with a magnetic stirrer and a reflux condenser, were placed the compound (5) obtained in the Synthesis Example 5 (18.73 g) and methyl glycidyl ether (13.60 g) in methanol (50 ml), and the mixture was refluxed overnight. The solvent was evaporated, and the resultant yellow oil was distilled under reduced pressure (bp.: 142°–145° C./7.5×10$^{-3}$ mmHg) to yield 22.70 g of a purified pale yellow product (yield 82%).

Through analysis by $^1$H-NMR, the purified product was identified to be 5-methyl-N-(2-hydroxy-3-methoxypropyl)-N-phenyl-2-furanmethane amine (compound (13)).

$^1$H-NMR (CDCl$_3$, δ): 7.16–7.25 (m, 2H), 6.72–6.88 (m,2H), 6.68–6.70 (m, 1H), 6.01 (d, 1H, J=3.0 Hz), 5.85 (d, 1H, J=3.0 Hz), 4.44 (s, 2H), 4.03–4.09 (m, 1H), 3.35–3.51 (m, 4H), 3.38 (s, 3H), 2.69 (d, 1H, J=4.0 Hz), 2.24 (s, 3H).

ps Synthesis Example 13:

Into a 500-ml two-necked flask equipped with a magnetic stirrer, a reflux condenser, and a 25-ml dropping funnel were placed 5-methylfurfural (33.10 g), p-anisidine (40.20 g), and acetic acid (18.28 g) in methanol (200 ml), and the mixture was then cooled on ice. Sodium cyanoborohydride (7.06 g) in methanol (10 ml) was added to the flask dropwise over approximately 10 minutes. After completion of addition, the mixture was stirred for 30 minutes with cooling on ice, and then refluxed overnight. The flask was cooled, and then the solvent was evaporated. The resultant yellow oil was dissolved in chloroform (200 ml). The solution was successively washed using a 2N aqueous NaOH solution and brine, after which the solvent was evaporated to give a yellow oil. The resultant yellow oil was distilled under reduced pressure (bp.: 135°–139° C./1.0×10$^{-2}$ mmHg) to yield 54.11 g of a purified pale yellow product (yield 83%).

Into a 100-ml round-bottomed flask equipped with a magnetic stirrer and a reflux condenser, were placed the purified pale yellow product obtained in the above step (21.77 g) and methyl glycidyl ether (17.90 g) in methanol (50 ml), and the mixture was refluxed overnight. The solvent was evaporated, and the resultant yellow oil was distilled under reduced pressure (bp.: 161°–162° C./7.6×10$^{-3}$ mmHg) to yield 24.95 g of a purified pale yellow product (yield 82%).

Through analysis by $^1$H-MMR, the purified product was identified to be 5-methyl-N-(2-hydroxy-3-methoxypropyl)-N-(4-methoxyphenyl)-2-furanmethane amine (compound (14).

$^1$H-NMR (CDCl$_3$, δ): 6.85 (d, 2H, J=3.0 Hz), 6.81 (d, 2H, J=3.0 Hz), 5.97 (d, 1H, J=3.0 Hz), 5.84 (d, 1H, J=3.0 Hz), 4.32 (s, 2H), 3.93–4.00 (m, 1H), 3.74 (s, 3H), 3.37 (s, 3H), 3.20–3.49 4H), 2.85 (bs, 1H), 2.24 (s, 3H).

Synthesis Example 14:

Into a 300-ml two-necked flask equipped with a magnetic stirrer, a reflux condenser, and a 25-ml dropping funnel were placed 5-methylfurfural (22.02 g), 3,4,5-trimethoxyaniline (36.64 g), and acetic acid (12.01 g) in methanol (200 ml), and the flask and its contents were then cooled on ice. Sodium cyanoborohydride (5.03 g) in methanol (10 ml) was added to the flask dropwise over approximately 10 minutes. After completion of addition, the mixture was starred for 30 minutes with cooling on ice, and stirred for a further 3 hours at room temperature. The solvent was evaporated, and the resultant yellow oil was dissolved in chloroform (200 ml). The resultant solution was successively washed using a 2N aqueous NaOH solution and brine, after which the solvent evaporated to give a yellow oil. The resultant yellow oil was distilled under reduced pressure (bp.: 139°–141° C./2.3×10$^{-3}$ mmHg) to yield 51.49 g of a purified pale yellow product (yield (93%).

Into a 100-ml round-bottomed flask equipped with a magnetic stirrer and a reflux condenser were placed the purified pale yellow product obtained in the above step (27.73 g) and methyl glycidyl ether (13.22 g) in methanol (50 ml), and the resulting mixture was refluxed overnight. The solvent was evaporated to yield a yellow oil. The resultant yellow oil was purified by silica gel column chromatography (solvents: hexane 4+ethylacetate 1) to obtain 29.80 g of a purified yellow product (yield: 82%).

Through analysis by $^1$H-NMR, the purified product was identified to be 5-methyl-N-(2-hydroxy-3-methoxypropyl)-N-(3,4,5-trimethoxyphenyl)-2-furanmethane amine (compound (15)).

$^1$H-NMR (CDCl$_3$, δ): 6.15 (s, 2H), 6.06 (d, 2H, J=3.0 Hz), 5.88 (d, 2H, J=3.0 Hz), 4.40 (d, 2H, J=2.5 Hz), 3.83 (s, 6H), 3.77 (s, 3H), 3.30–3.50 (m, 4H), 3.40 (s, 3H), 2.65 (d, 1H, J=4.0 Hz), 2.26 (s, 3H).

Synthesis Example 15:

Into a 100-ml two-necked flask equipped with a magnetic stirrer, a reflux condenser, and a 25-ml dropping funnel were placed 5-methylfurfural (5.54 g), p-toluidine (5.71 g), and acetic acid (3.05 g) in methanol (50 ml), and the mixture was then cooled on ice. Sodium cyanoborohydride (1.28 g) in methanol (10 ml) was added to the flask dropwise over approximately 10 minutes. After completion of addition, the mixture was stirred for 30 minutes with cooling on ice, and refluxed further overnight. The flask was allowed to cool, and then the solvent was evaporated. The resultant yellow oil was dissolved in chloroform (50 ml). The solution was successively washed using a 2N aqueous NaOH solution and brine, after which the solvent was evaporated to give a yellow oil. The resultant yellow oil was distilled under reduced pressure (bp.: 104°–106° C./7.6×10$^{-3}$ mmHg) to yield 6.33 g of a purified yellow product (yield 63%).

Into a 100-ml round-bottomed flask equipped with a magnetic stirrer and a reflux condenser were placed the purified yellow product obtained in the above step (6.33 g) and methyl glycidyl ether (6.02 g) in methanol (25 ml), and the resulting mixture was refluxed overnight. The solvent was evaporated to give a yellow oil. The resultant yellow oil was purified by silica gel column chromatography (solvents: hexane 4+ethyl acetate 1) to obtain 6.83 g of a purified yellow product (yield: 75%).

Through analysis by $^1$H-NMR, the purified product was identified to be 5-methyl-N-(2-hydroxy-3-methoxypropyl)-N-(4-methylphenyl)-2-furanmethane amine (compound (16)).

$^1$H-NMR (CDCl$_3$, δ): 7.02 (d, 2H, J=8.6 Hz), 6.78 (d, 2H, J=8.6 Hz), 5.99 (d, 1H, J=3.0 Hz), 5.84 (d, 1H, J=3.0 Hz), 4.40 (s, 2H), 4.02–4.13 (m, 1H), 3.38 (s, 3H), 3.27–3.53 (m, 4H), 2.72 (d, 1H, J=4.2 Hz), 2.23 (s, 6H).

Synthesis Example 16:

Into a 300-ml two-necked flask equipped with a magnetic stirrer, a reflux condenser, and a 50-ml dropping funnel were placed 5-methylfurfural (28.87 9), o-toluidine (28.08 g), and acetic acid (15.78 g) in methanol (200 ml), and the mixture was then cooled on ice. Sodium cyanoborohydride (6.58 g) in methanol (20 ml) was added to the flask dropwise over approximately 10 minutes. After completion of addition, the mixture was stirred for 30 minutes with cooling on ice, and stirred for a further 3 hours at room temperature. The solvent was evaporated, and the resultant yellow oil was dissolved in chloroform (100 ml). The solution was successively washed using a 2N aqueous NaOH solution and brine, after which the solvent was evaporated to give a yellow oil. The resultant yellow oil was distilled under reduced pressure (bp.: 113°–115° C./7.6×10$^{-3}$ mmHg) to yield 38.19 g of a purified yellow product (yield 72%).

Into a 200-ml round-bottomed flask equipped with a magnetic stirrer and a reflux condenser were placed the purified yellow product obtained in the above step (38.19 g) and methyl glycidyl ether (27.86 g) in methanol (50 ml), and the resulting mixture was refluxed overnight. The solvent was evaporated to give a yellow oil. The resultant yellow oil was distilled under reduced pressure (bp.: 142°–145° C./7.5×10$^{-3}$ mmHg) to yield 33.32 g of a purified yellow product (yield 61%)

Through analysis by $^1$H-NMR, the purified product was identified to be 5-methyl-N-(2-hydroxy-3-methoxypropyl)-N)-2-methylphenyl)-2-furanmethane amine (compound (17)).

$^1$H-NMR (CDCl$_3$, δ): 6.98–7.25 4H), 5.90 (d, 1H, J=3.0 Hz), 5.84 (d, 1H, J=3.0 Hz), 3.95 (s, 2H), 3.42–3.84 1H), 3.31 (s, 3H), 3.18–3.43 (m, 4H), 2.96–3.01 (m, 2H), 2.35 (s, 3H), 2.25 (s, 3H).

Synthesis Example 17:

Into a 300-ml two-necked flask equipped with a magnetic stirrer, a reflux condenser, and a 50-ml dropping funnel were placed 5-methylfurfural (22.20 g), 5-amino-o-cresol (25.44 g), and acetic acid (12.05 g) in ethanol (200 ml), and the mixture was then cooled on ice. Sodium cyanoborohydride (5.05 g) in ethanol (20 ml) was added to the flask dropwise over approximately 10 minutes. After completion of addition, the mixture was stirred for 30 minutes with cooling on ice, and stirred for a further 4 hours at room temperature. The solvent was evaporated, and the resultant yellow oil was dissolved in chloroform (100 ml). The resultant solution was successively washed using a 2N aqueous NaOH solution and brine, after which the solvent was evaporated to give a yellow oil. The resultant yellow oil was distilled under reduced pressure (bp.: 162°–168° C./7.8×10$^{-3}$ mmHg) to yield 23.62 g of a purified yellow product (yield 54%).

Into a 200-ml round-bottomed flask equipped with a magnetic stirrer and a reflux condenser were placed the purified yellow product obtained in the above step (23.62 g) and methyl glycidyl ether (21.17 g) in methanol (50 ml), and the resulting mixture was refluxed overnight. The solvent was evaporated to yield a yellow oil. The yellow oil was purified by silica gel column chromatography (solvents: hexane 3+ethyl acetate 1) to obtain 26.89 g of a purified yellow product (yield: 81%).

Through analysis by $^1$H-NMR, the purified product was identified to be 5-methyl-N-(2-hydroxy-3-methoxypropyl)-N-(2-hydroxy-3-methylphenyl)-2-furanmethane amine (compound (18 ) ).

$^1$H-NMR (CDCl$_3$, δ): 6.90–6.95 (m, 1H), 6.34–6.40 (m, 2H), 6.00 (d, 1H, J=3.0 Hz), 5.85 (d, 1H, J=3.0 Hz), 5.03 (s, 1H), 4.39 (s, 2H), 4.03–4.15 (m, 1H), 3.34–3.55 (m, 4H), 3.39 (s, 3H), 2.72 (d, 1H, J=3.7 Hz), 2.24 (s, 3H), 2.13 (s, 3H), 1.70 (s, 1H).

Synthesis Example 18:

Into a 500-ml round-bottomed flask equipped with a magnetic stirrer and a reflux condenser were placed the compound (5) obtained in Synthesis Example 5 (37.45 g) and freshly distilled glycidol (29.63 g) in methanol (200 ml), and the mixture was refluxed overnight. The solvent was evaporated, and the resultant pale yellow oil was purified by silica gel column chromatography (solvents: hexane 3+ethyl acetate 1) to obtain 49.12 g of a purified pale yellow product (yield: 94%).

Through analysis by $^1$H-NMR, the purified product was identified to be 5-methyl-N-(2,3-dihydroxypropyl)-N-phenyl-2-furanmethane amine (compound (19)).

$^1$H-NMR (CDCl$_3$, δ): 7.10–7.30 (m, 2H), 6.70–7.91 (m, 3H), 6.03 (d, 1H, J=3.0 Hz), 5.86 (d, 1H, J=3.0 Hz), 4.43 (s, 2H), 4.00 (bs, 1H), 3.30–3.70 (m, 4H), 2.80 (bs, 1H), 2.24 (s, 3H).

Synthesis Example 19:

Into a 200-ml two-necked flask equipped with a magnetic stirrer, a reflux condenser, and a 25-ml dropping funnel were placed 5-methylfurfural (12.13 g), p-aminophenethyl alcohol (13.73 g), and acetic acid (6.05 g) in ethanol (100 ml), and the mixture was then cooled on ice. Sodium cyanoborohydride (2.53 g) in ethanol (10 ml) was added to the flask dropwise over approximately 10 minutes. After completion of addition, the mixture was stirred for 30 minutes with cooling on ice, and stirred for a further 4 hours at room temperature. The solvent was evaporated, and the resultant reddish yellow oil was dissolved in chloroform (200 ml). The resultant solution was successively washed using a 2N aqueous NaOH solution and brine, after which the solvent was evaporated to give a yellow oil. The resultant yellow oil was purified by silica gel column chromatography (solvents: hexane 3+ethyl acetate 1) to obtain 17.83 g of a purified yellow product (yield: 77%).

Into a 200-ml round-bottomed flask equipped with a magnetic stirrer and a reflux condenser were placed the purified yellow product obtained in the above step (13.02 g) and methyl glycidyl ether (21.17 g) in methanol (50 ml), and the resulting mixture was refluxed overnight. The solvent was evaporated to give a yellow oil. The resultant yellow oil was purified by silica gel column chromatography (solvents: hexane 2+ethyl acetate 1) to obtain 18.21 g of a purified yellow product (yield: 74%).

Through analysis by $^1$H-NMR, the purified product was identified to be 5-methyl-N-(2-hydroxy-3-methoxypropyl)-N-(p-(2-hydroxyethyl)phenyl))-2-furanmethane amine (compound (20 ).

$^1$H-NMR (CDCl$_3$, δ): 7.04 (d, 2H, J=8.6 Hz), 6.80 (d, 2H, J=8.6 Hz), 5.95 (d, 1H, J=3.0 Hz), 5.86 (d, 1H, J=3.0 Hz), 4.37 (s, 2H), 4.00–4.20 (m, 1H 3.93 (d, 1H , J=5.2 Hz), 3.74 (dt, 2H, J=6.7, 7.3 Hz), 3.27–3.50 (m, 4H), 3.36 (s, 3H), 2.78 (t, 1H, J=7.3 Hz), 2.72 (t, 2H, J=6.7 Hz), 2.22 (s, 3H).

Synthesis Example 20:

Into a 200-ml two-necked flask equipped with a magnetic stirrer, a reflux condenser, and a 50 -ml dropping funnel were placed 5-methylfurfural (24–20 g), aminoethanol (6.13 g), and acetic acid (6.15 g) in methanol (100 ml), and the mixture was then cooled on ice. Sodium cyanoborohydride (9.43 g) in methanol (20 ml) was added to the flask dropwise over approximately 10 minutes. After completion of addition, the mixture was stirred for 30 minutes with cooling on ice, and stirred for a further 2 hours at room temperature. The solvent was evaporated, and the resultant yellow oil was dissolved in chloroform (100 ml). The resultant solution was successively washed using a 2N aqueous NaOH solution and brine, after which the solvent was evaporated to give a yellow oil. The resultant yellow oil was distilled under reduced pressure (bp.: 117°–121° C./7.3×10$^{-3}$ mmHg) to yield 19.96 g of a purified pale yellow product (yield 80%).

Through analysis by $^1$H-NMR, the purified product was identified to be N,N-bis(5-methylfurfuryl)ethanolamine (compound (21)).

$^1$H-NMR (CDCl$_3$, δ): 6.08 (d, 2H, J=2.9 Hz), 5.89 (d, 2H, J=2.9 Hz), 3.65 (s, 4H, 3.57 (t, 2H, J=5.4 Hz) 2.81 (bs, 1H), 2.69 (t, 2H, J=5.4 Hz), 2.28 (s, 6H).

Synthesis Example 21:

Into a 200-ml two-necked flask equipped with a magnetic stirrer, a reflux condenser, and a 25-ml dropping funnel were placed furfural (20.56 g), n-butylamine (7.36 g), and acetic acid (6.02 g) in methanol (100 ml), and the mixture was then cooled on ice. Sodium cyanoborohydride (5.10 g) in methanol (10 ml) was added to the flask dropwise over approximately 10 minutes. After completion of addition, the mixture was stirred for 30 minutes while cooling on ice, and stirred for a further 2 hours at room temperature. The solvent was evaporated, and the resultant yellow oil was dissolved in chloroform (100 ml). The resultant solution was successively washed using a 2N aqueous NaOH solution and brine, after which the solvent was evaporated to give a yellow oil. The resultant yellow oil was distilled under reduced pressure (bp.: 87°–89° C./1×10$^{-3}$ mmHg) to yield 18.34 g of a purified pale yellow product (yield 78%).

Through analysis by $^1$H-NMR, the purified product was identified to be N,N-bisfurfurylbutylamine (compound (22)).

$^1$ H-NMR (CDCl$_3$, δ): 7.38 (dd, 2H, J=0.7, 1.9 Hz), 6.32 (dd, 2H, J=1.9, 3.1 Hz), 6.20 (dd, 2H, J=0.7, 3.1 Hz), 3.65 (s, 4H), 2.39–2.47 (m, 2H), 1.24–1.60 (m, 4H), 0.89 (t, 3H, J=7.2 Hz).

Synthesis Example 22:

Into a 200-ml two-necked flask equipped with a magnetic stirrer, a reflux condenser, and a 25-ml dropping funnel were placed furfural (3.84 g), 2-ethylhexylamine (2.59 g), and acetic acid (1.20 g) in methanol (80 ml), and the mixture was then cooled on ice, Sodium cyanoborohydaride (1.01 g) in methanol (10 ml) was added to the flask dropwise over approximately 10 minutes. After completion of addition, the mixture was stirred for 30 minutes with cooling on ice, and stirred for a further 2 hours at room temperature. The solvent was evaporated, and the resultant yellow oil was dissolved in chloroform (50 ml). The resultant solution was successively washed using a 2N aqueous NaOH solution and brine, after which the solvent was evaporated to give a yellow oil. The resultant yellow oil was distilled under reduced pressure (bp.: 102°–104° C./5.5×10$^{-3}$ mmHg) to yield 3.03 g of a purified pale yellow product (yield 53%).

Through analysis by $^1$H-NMR, the purified product was identified to be N,N-bisfurfuryl-2-ethylhexylamine (compound (23)).

$^1$H-NMR (CDCl$_3$, δ): 7.38 (dd, 2H, J=0.7, 1.9 Hz), 6.32 (dd, 2H, J=1.9, 3.1 Hz), 6.19 (dd, 2H, J=0.7, 3.1 Hz), 3.64 (s, 4H), 2.25 (d, 2H, J=7.1 Hz), 0.60–1.70 (m, 15H).

Synthesis Example 23:

Into a 200-ml two-necked flask equipped with a magnetic stirrer, a reflux condenser, and a 25-ml dropping funnel were placed furfural (9.81 g) and glycine ethyl ester hydrochloride (7.11 g) in methanol (100 ml), and the mixture was then cooled on ice. Sodium cyanoborohydride (2.53 g) in methanol (10 ml) was added to the flask dropwise over approximately 10 minutes. After completion of addition, the mixture was stirred for 30 minutes with cooling on ice, and then refluxed for 2 hours. The flask was allowed to cool, and then the solvent was evaporated, and the resultant yellow oil was dissolved in chloroform (100 ml). The resultant solution was successively washed using a 2N aqueous NaOH solution and brine, after which the solvent was evaporated to give a yellow oil. The resultant yellow oil was purified by silica gel column chromatography (solvents: hexane 4+ethyl acetate 1) to obtain 8.93 g of a purified, pale yellow product (yield: 60%).

Through analysis by $^1$H-NMR, the purified product was identified to be ethyl N,N-bisfurfurylglycine (compound (24)).

$^1$H-NMR (CDCl$_3$, δ): 7.39 (dd, 2H, J=0.8, 1.8 Hz), 6.32 (dd, 2H, J=1.8, 3.1 Hz), 6.24 (dd, 2H, J=0.8, 3.1 Hz), 4.16 (q, 2H, J=7.1 Hz), 3.85 (s, 4H), 3.35 (s, 2H), 1.27 (t, 3H, J=7.1 Hz).

Synthesis Example 24:

Into a 200-ml two-necked flask equipped with a magnetic stirrer, a reflux condenser, and a 50-ml dropping funnel were placed 5-methylfurfural (26.40 g), aniline (9.31 9), and acetic acid (6.01 g) in methanol (100 ml), and the mixture was then cooled on ice. Sodium cyanoborohydride (8.80 g) in methanol (20 ml) was added to the flask dropwise over approximately 10 minutes. After completion of addition, the mixture was stirred for 30 minutes while cooling on ice, and refluxed further overnight. The flask was allowed to cool, and then the solvent was evaporated, and the resultant dark brown oil was dissolved in chloroform (100 ml). The resultant solution was successively washed using a 2N aqueous NaOH solution and brine, after which the solvent was evaporated to give a dark brown oil. The dark brown oil was distilled under reduced pressure (bp.: 130°–132° C./5.0×10$^{-3}$ mmHg) to yield 13.42 g of a purified yellow product (yield 48%).

Through analysis by $^1$H-NMR, the purified product was identified to be N,N-bis(5-methylfurfuryl)phenylamine (compound (25)).

$^1$H-NMR (CDCl$_3$, δ): 7.10–7.30 (m, 2H), 6.70–7.00 (m, 3H), 6.03 (d, 2H, J=3.0 Hz), 5.87 (d, 2H, J=3.0 Hz), 4.44 (s, 4H), 2.26 (s, 6H).

Synthesis Example 25:

Into a 100-ml two-necked flask equipped with a magnetic stirrer, a reflux condenser, and a 25-ml dropping funnel were placed 5-methylfurfural (4.40 g), p-anisidine (2.46 g), and acetic acid (1.20 g) in methanol (50 ml), and the mixture was then cooled on ice. Sodium cyanoborohydride (1.01 g) in methanol (10 ml) was added to the flask dropwise over approximately 10 minutes. After completion of addition, the mixture was stirred for 30 minutes-with cooling on ice, and refluxed further overnight. The flask was allowed to cool, and then the solvent was evaporated, and the resultant dark brown oil was dissolved in chloroform (100 ml). The resultant solution was successively washed using a 2N aqueous NaOH solution and brine, after which the solvent was evaporated to give a dark brown oil. The dark brown oil was distilled under reduced pressure (bp.: 119°–123° C./4.3×10$^{-3}$ mmHg) to yield 3.07 g of a purified yellow product (yield 49%).

Through analysis by $^1$H-NMR, the purified product was identified to be N,N-bis(5-methylfurfuryl)-p-methoxyphenylamine (compound (26)).

$^1$H-NMR (CDCl$_3$, δ): 6.89 (d, 2H, J=9.3 Hz), 6.79 (d, 2H, J=9.3 Hz), 6.00 (d, 2H, J=3.0 Hz), 5.86 (d, 2H, J=3.0 Hz), 4.33 (s, 4H), 3.75 (s, 3H), 2.26 (s, 6H).

Synthesis Example 26:

Into a 100-ml two-necked flask equipped with a magnetic stirrer, a reflux condenser, and a 25-ml dropping funnel were placed 5-methylfurfural (4.40 g), 3,4-dimethoxyaniline (3.06 g), and acetic acid (1.20 g) in methanol (50 ml), and the mixture was cooled on ice. Sodium cyanoborohydride (1.01 g) in methanol (10 ml) was added to the flask dropwise over approximately 10 minutes. After completion of addition, the mixture was stirred for 30 minutes with cooling on ice, and refluxed further overnight. The flask was allowed to cool, and then the solvent was evaporated, and the resultant dark brown oil was dissolved in chloroform (100 ml). The resultant solution was successively washed using a 2N aqueous NaOH solution and brine, after which the solvent was evaporated to give a dark brown oil. The resultant dark brown oil was purified by silica gel column chromatography (solvents: hexane 4+ethyl acetate 1) to obtain 2.41 g of a purified yellow product (yield: 35%).

Through analysis by $^1$H-NMR, the purified product was identified to be N,N-bis(5-methylfurfuryl)-3,4-dimethoxyphenylamine (compound (27)).

$^1$H-NMR (CDCl$_3$, δ): 6.76 (d, 1H, J=8.7 Hz), 6.64 (d, 1H, J=2.8 Hz), 6.44 (dd, 1H, J=2.8, 8.7 Hz) 6.03 (d, 2H, J=3.0 Hz), 5.87 (d, 2H, J=3.0 Hz), 4.34 (s, 4H), 3.84 (s, 3H), 3.81 (s, 3H,), 2.26 (s, 6H).

Synthesis Example 27:

Into a 100-ml two-necked flask equipped with a magnetic stirrer, a reflux condenser, and a 25-ml dropping funnel were placed 5-methylfurfural (4.40 g), 3,4,5-trimethoxyaniline (3.66 g), and acetic acid (1.20 g) in methanol (50 ml), and the mixture was cooled on ice. Sodium cyanoborohydride (1.01 g) in methanol (10 ml) was added to the flask dropwise over approximately 10 minutes. After completion of addition, the mixture was stirred for 30 minutes with cooling on ice, and refluxed further overnight. The flask was allowed to cool, and then the solvent was evaporated, and the resultant dark brown oil was dissolved in chloroform (100 ml). The resultant solution was successively washed using a 2N aqueous NaOH solution and brine, after which the solvent was evaporated to give a dark brown oil. The resultant dark brown oil was purified by silica gel column chromatography (solvents: hexane 4+ethyl acetate 1) to obtain 1.63 g of a purified yellow product (yield: 22%).

Through analysis by $^1$H-NMR, the purified product was identified to be N,N-bis(5-methylfurfuryl)-3,4,5-trimethoxyphenylamine (compound (28)).

$^1$H-NMR (CDCl$_3$, δ): 6.22 (s, 2H), 6.07 (d, 2 H, J=3.0 Hz), 5.89 (d, 2H, J=3.0 Hz), 4.39 (s, 4H), 3.83 (s, 6H), 3.77 (s, 3H), 2.27 (s, 6H).

Synthesis Example 28:

Into a 100-ml two-necked flask equipped with a magnetic stirrer, a reflux condenser, and a 25-ml dropping funnel were placed 5-methylfurfural (4.40 g), p-toluidine (2.41 g), and acetic acid (1.20 g) in methanol (50 ml), and the mixture was cooled on ice. Sodium cyanoborohydride (1.01 g) in methanol (10 ml) was added to the flask dropwise over approximately 10 minutes. After completion of addition, the mixture was stirred for 30 minutes with cooling on ice, and refluxed further overnight. The flask was allowed to cool, and then the solvent was evaporated, and the resultant dark brown oil was dissolved in chloroform (100 ml). The resultant solution was successively washed using a 2N aqueous NaOH solution and saturated brine, after which the solvent was evaporated to give a dark brown oil. The resultant dark brown oil was distilled under reduced pressure (bp.: 144°–149° C./3.0×10$^{-3}$ mmHg) to yield 1.90 g of a purified yellow product (yield 32%).

Through analysis by $^1$H-NMR, the purified product was identified to be N,N-bis(5-methylfurfuyl)-4-methylphenylamine (compound (29)).

$^1$H-NMR (CDCl$_3$, δ): 7.02 (d, 2H, J=8.7 Hz), 6.83 (d, 2H, J=8.7 Hz), 6.01 (d, 2H, J=3.1 Hz), 5.85 (d, 2H, J=3.1 Hz), 4.40 (s, 4H), 2.25 (s, 6H), 2.24 (s, 3H).

Synthesis Example 29:

Into a 100-ml two-necked flask equipped with a magnetic stirrer, a reflux condenser, and a 25-ml dropping funnel were placed 5-methylfurfural (4.40 g), o-toluidine (2.41 g), and acetic acid (acetic acid (1.20 g) in methanol (50 ml), and cooled on ice. Sodium cyanoborohydride (1.01 g) in methanol (10 ml) was added to the flask dropwise over approximately 10 minutes. After completion of addition, the mixture was stirred for 30 minutes with cooling on ice, and refluxed overnight. The flask was allowed to cool, and then the solvent was evaporated, and the resultant dark brown oil was dissolved in chloroform (100 ml). The resultant solution was successively washed using a 2N aqueous NaOH solution and brine, after-which the solvent was evaporated to give a dark brown oil. The resultant dark brown oil was purified by silica gel column chromatography (solvents: hexane 4+ethyl acetate 1) to obtain 1.08 g of a purified yellow product (yield: 18%).

Through analysis by $^1$H-NMR, the purified product was identified to be N,N-bis(5-methylfurfuryl)-2-methylphenylamine (compound (30)).

$^1$H-NMR (CDCl$_3$, δ): 6.90–7.20 (m, 4H), 5.93 (d, 2H, J=3.0 Hz), 5.83 (d, 2H, J=3.0 Hz), 4.05 (s, 4H), 2.36 s, 3H), 2.23 (s, 6H).

Synthesis Example 30:

Into a 500-ml two-necked flask equipped with a magnetic stirrer, a reflux condenser, and a 50-ml dropping funnel were placed 5-methylfurfural (33.10 g), p-anisidine (40.20 g), and acetic acid (18.28 g) in methanol (200 ml), and the mixture was cooled on ice. Sodium cyanoborohydride (7.06 g) in methanol (30 ml) was added to the flask dropwise over approximately 10 minutes. After completion of addition, the mixture was stirred for 30 minutes with cooling on ice, and stirred for a further 4 hours at room temperature. The solvent was evaporated, and the resultant yellow oil was dissolved in chloroform (300 ml). The resultant solution was successively washed using a 2N aqueous NaOH solution and brine, after which the solvent was evaporated to give a yellow oil. The resultant yellow oil was distilled under reduced pressure (bp.: 133°–139° C./1.0×10$^{-3}$ mmHg) to yield 54.11 g of a purified product (yield 83%).

Subsequently, into a 100-ml two-necked flask equipped with a magnetic stirrer, a reflux condenser, and a 10-ml dropping funnel were placed the purified product obtained in the above step (4.11 g), furfural (1.92 g), and acetic acid (1.20 g) in methanol (50 ml), and the mixture was cooled on ice. Sodium cyanoborohydride (0.63 g) in methanol (5 ml) was added to the flask dropwise over approximately 10 minutes. After completion of addition, the mixture was stirred for 30 minutes with cooling on ice, and refluxed further overnight. The flask was allowed to cool, and then the solvent was evaporated, and the resultant dark brown oil was dissolved in chloroform (100 ml). The resultant solution was successively washed using a 2N aqueous NaOH solution and brine, after which the solvent was evaporated to give a dark brown oil. The resultant dark brown oil was purified by silica gel column chromatography (solvents: hexane 4+ethyl acetate 1) to obtain 2.99 g of a purified yellow product (yield: 50%).

Through analysis by $^1$H-NMR, the purified product was identified to be N-furfuryl-N-(5-methylfurfuryl)-4-methoxyphenylamine (compound (31)).

$^1$H-NMR (CDCl$_3$, δ): 7.35 (dd, 1H, J=0.6, 1.8 Hz), 6.89 (d, 2H, J=9.3 Hz), 6.80 (d, 2H, J=9.3 Hz), 6.29 (dd, 1H, J=1.8, 3.2 Hz), 6.12 (dd, 1H, J=0.6, 3.2 Hz), 6.01 (d, 1H, J=3.0 Hz), 5.86 (d, 1H, J=3.0 Hz), 4.39 (s, 2H), 4.33 (s, 2H), 3.75 (s, 3H), 2.26 (s, 3H).

Synthesis Example 31:

Into a 200-ml round-bottomed flask equipped with a magnetic stirrer and a reflux condenser were placed 3,4-xylidine (24.24 g), methyl glycidyl ether (17.62 g), and methanol (50 ml), and the mixture was refluxed overnight. The solvent was evaporated, and the resultant yellow oil was distilled under reduced pressure to yield 23.00 g of a pale yellow intermediate (yield: 55%).

into a 200-ml two-necked flask equipped with a magnetic stirrer, a reflux condenser, and a 25-ml dropping funnel were placed the pale yellow intermediate obtained-in the above step (10.46 g), n-butyraldehyde (5.41 g), acetic acid (3.00 g), and methanol (100 ml), and the mixture was cooled on ice. Sodium cyanoborohydride (1.89 g) in methanol (10 ml) was added to the flask dropwise over approximately 10 minutes. After completion of addition, the mixture was stirred for 30 minutes with cooling on ice, and stirred for a further 4 hours at room temperature. The solvent was evaporated, and the resultant pale yellow oil was dissolved in ethyl acetate (100 ml). The resultant solution was successively washed using a 2N aqueous NaOH solution and brine, after which the solvent was evaporated to give a pale yellow oil. The resultant pale yellow oil was purified by silica gel column chromatography (solvents: hexane 5+ethyl acetate 1) to obtain 11.36 g of a purified colorless product (yield: 86%).

Through analysis by $^1$H-NMR, the purified product was identified to be N-n-butyl-N-(2-hydroxy-3-methoxypropyl)-3,4-xylidine (compound (32)).

$^1$H-NMR (CDCl$_3$, δ): 0.93 (t, 3H, J=7.2 Hz), 1.23–1.41 (m, 2H), 1.46–1.61 (m, 2H), 2.16 (s, 3H), 2.22 (s, 3H), 2.30–2.70 (bs, 1H), 3.20–3.51 (m, 6H), 3.40 (s, 3H), 3.95–4.13 (m, 1H) 6.51–6.60 (m, 2H), 6.98 (d, 1H, J=8.1 Hz).

Synthesis Example 32:

Into a 200-ml round-bottomed flask equipped with a magnetic stirrer and a reflux condenser were placed p-toluidine (21.43 g), glycidol (14.82 g), and methanol (50 ml), and the mixture was refluxed overnight. The solvent was evaporated, and the resultant pale yellow oil was distilled under reduced pressure to yield 20.21 g of a white crystalline intermediate (mp.: 71.9° C.) (yield: 56%).

Into a 200-ml two-necked flask equipped with a magnetic stirrer, a reflux condenser, and a 25-ml dropping funnel were placed the white crystalline intermediate obtained in the above step (10.87 g), 35% formalin solution (7.72 g), acetic acid (3.60 g), and methanol (100 ml), and the mixture was cooled on ice. Sodium cyanoborohydride (2.26 g) in methanol (10 ml) was added to the flask dropwise over approximately 10 minutes. After completion of addition, the mixture was stirred for 30 minutes with cooling on ice, and stirred for a further 4 hours at room temperature. The solvent was evaporated, and the resultant yellow oil was dissolved in ethyl acetate (100 ml). The resultant solution was successively washed using a 2N aqueous NaOH solution and brine, after which the solvent was evaporated to give a pale yellow oil. The resultant pale yellow oil was purified by silica gel column chromatography (solvents: hexane 1+ethyl acetate 1) to obtain 8.96 g of a purified pale yellow product (yield: 76%).

Through analysis by $^1$H-NMR, the purified product was identified to be N-(2,3-dihydroxypropyl)-N-methyl-p-toluidine (compound (33)).

$^1$H-NMR (CDCl$_3$, δ): 2.15 (bs, 2H), 2.26 (s, 3H), 2.91 (s, 3H), 3.22 (dd, 1H, J=5.0, 14.5 Hz), 3.38 (dd, 1H, J=8.2, 14.5 Hz), 3.56 (dd, 1H, J=5.4, 11.5 Hz), 3.78 (dd, 1H, J=3.2, 11.5 Hz), 3.95–4.03 (m, 1H), 6.75 (d, 2H, J=8.4 Hz), 7.06 (d, 2H, J=8.4 Hz).

Synthesis Example 33:

Into a 200-ml round-bottomed flask equipped with a magnetic stirrer and a reflux condenser were placed 3,4-xylidine (24.24 g), glycidol (16.30 g), and methanol (50 ml), and the mixture was refluxed overnight. The solvent was evaporated, and the resultant yellow crystals were recrystallized to yield 22.06 g of a white crystalline intermediate (mp.: 97.8° C.) (yield: 56%).

Into a 200-ml two-necked flask equipped with a magnetic stirrer, a reflux condenser, and a 25-ml dropping funnel were placed the white crystalline intermediate obtained in the above step (9.76 g), n-butyraldehyde (5.41 g)., acetic acid (3.00 g), and methanol (100 ml), and the mixture was cooled on ice. Sodium cyanoborohydride (1.89 g) in methanol (10 ml) was added to the flask dropwise over approximately 10 minutes. After completion of addition, the mixture was stirred for 30 minutes with cooling on ice, and stirred for a further 4 hours at room temperature. The solvent was evaporated, and the resultant yellow oil was dissolved in ethyl acetate (100 ml). The resultant solution was successively washed using a 2N aqueous NaOH solution and brine, after which the solvent was evaporated to give pale yellow crystals. The pale yellow crystals were purified by recrystallization to obtain 9.29 g of purified white crystals (mp.: 70.0° C.) (yield: 74%).

Through analysis by $^1$H-NMR, the purified white crystalline product was identified to be N-n-butyl-N-(2,3-dihydroxypropyl)-3,4-xylidine (compound (34)).

$^1$H-NMR (CDCl$_3$, δ): 0.92 (t, 3H, J=7.1 Hz), 1.26–1.40 (m, 2H), 1.41–1.56 (m, 2H), 2.17 (s, 3H), 2.22 (s, 3H), 2.49 (bs, 1H), 2.86 (bs, 1H), 3.19–3.34 (m, 4H), 3.53 (dd, 1H, J=5.3, 11.4 Hz), 3.75 (dd, 1H, J=3.2, 11.4 Hz), 3.91–3.96 (m, 1H), 65.4–6.63 (m, 2H), 6.98 (d, 1H, J=8, 1Hz).

Synthesis Example 34:

Into a 200-ml round-bottomed flask equipped with a magnetic stirrer and a reflux condenser were placed p-anisidine (24.63 g), glycidol (14.82 g), and methanol (50 ml), and the mixture was refluxed overnight. The solvent was evaporated, and the resultant yellow oil was distilled under reduced pressure to yield 17.40 g of a white crystalline intermediate (mp.: 71.5° C.) (yield: 48%).

Into a 200-ml two-necked flask equipped with a magnetic stirrer, a reflux condenser, and a 25-ml dropping funnel were placed the white crystalline intermediate obtained in the above step (10.87 g), n-octyl aldehyde (11.54 g), acetic acid (3.60 g), and methanol (100 ml), and the mixture was cooled on ice. Sodium cyanoborohydride (2.26 g) in methanol (10 ml) was added to the flask dropwise over approximately 10 minutes. After completion of addition, the mixture was stirred for 30 minutes with cooling on ice, and stirred for a further 4 hours at room temperature. The solvent was evaporated, and the resultant yellow oil was dissolved in ethyl acetate (100 ml). The resultant solution was successively washed using a 2N aqueous NaOH solution and brine, after which the solvent was evaporated to give a pale yellow oil. The resultant pale yellow oil was purified by silica gel column chromatography (solvents: hexane 5+ethyl acetate 1) to obtain 14.58 g of-a purified pale yellow product (yield: 79%).

Through analysis by $^1$H-NMR, the purified product was identified to be N-(2,3-dihydroxypropyl)-N-octyl-p-anisidine (compound (35)).

$^1$H-NMR (CDCl$_3$, δ): 0.87 (t, 3H, J=6.7 Hz), 1.10–1.62 (m, 12H), 2.23 (bs, 1H), 2.92 (bs, 1H), 3.10–3.21 (m, 4H), 3.53 (dd, 1H, J=4.8, 11.3 Hz), 3.73–3.89 (m, 2H), 3.77 (s-like, 4H), 6.84 (s-like, 4H).

Test Example 1

Method for measuring the quenching rate constant of singlet oxygen:

Apparatus

The apparatus used for measuring singlet oxygen included the following parts.

(1) Light source: Xenon lamp (150 W) (Atago Bussan K.K.)

(2) Filters on the excitation side: Water filter (optical path: 50 mm), Color glass filters (HA-15, HA-30, G-533, manufactured by Hoya K.K.)

(3) Sample: Square quartz cell (2×10×50 mm)

(4) Filters on the detection side: Color glass filter (IR-85, manufactured by Hoya K.K.), Interference filter (Nippon Shinku-Kogaku K.K.)

(5) Spectrometer and detector: Spectrometer (HR-320, Jovin Yvon Co.), Germanium (Ge) detector (EO-817L, a type using liquid nitrogen as a coolant, North coast Scientic Corporation)

(6) Amplifier: Light chopper (5584, NF Co.), Frequency filter (E-3201B, NF Co.), Super low noise amplifier (SA-200F3, NF Co.), Digital storage oscilloscope (2431L, SONY Tektronix Co.)

(7) Recording section: Personal computer (PC-9801 BA, NEC Corporation), GP-IB interface (8) Oxygen concentration control unit: High-pressure oxygen cylinder Using this apparatus, light was irradiated onto a system which is known to produce singlet oxygen through photochemical sensitization. The wavelength of the light was within an appropriate absorption range of the photosensitizer employed. weak emission in the near infrared region, which is specific to singlet oxygen, was measured for its intensity I. Subsequently, the emission obtained when a test substance was added to the same system was measured. From the decrease in emission intensity I, the quenching rate constant of singlet oxygen of the test substance could be measured in accordance with the Stern-Volmer method. However, since some substances react with the photochemical sensitization system to cause errors in the measurements, the method described by R. H. Young et al., *Photochem. Photobiol.*, vol. 17, p. 233 (1973) was applied to correct this contribution quenching.

Measuring Method

A 50 μM ethanol solution of Rose Bengal in a 400 μl square quartz cell was used as a test substance.

First, the light within 490–590 nm, which is appropriate for the maximum absorption wavelength of Rose Bengal, was irradiated onto the cell containing the test substance. The resulting emission Spectrum in the near infrared region showed a peak at 1,270 nm. This peak corresponds to the transition from singlet oxygen to ground state oxygen.

Similarly, another system was subjected to measurement in which a typical singlet oxygen quencher, β-carotene, sodium azide,or 1,4-diazabicyclo[2.2.2]octane, had been added. As a result, it was confirmed that as the concentration of the quencher increased, the peak at 1,270 nm weakened. From these results, this was determined to show the emission of singlet oxygen produced from the system using Rose Bengal as the photosensitizer.

Test Example 2:

Measurement of the quenching rate constant of singlet oxygen: An ethanol solution of each of compounds obtained in the above-described Synthesis Examples and N-phenyldiethanolamine (compound (36)), with Rose Bengal, as a conventional photosensitizer, was used for the measurement of the quenching rate constants of singlet oxygen.

First, emission intensity I of a mixture solution containing 50 μM of Rose Bengal and the above compounds were measured under saturated air conditions. The ratio $I_{Oair}/I_{air}$ was calculated, wherein $I_{air}$ represents the emission intensity measured for a solution with a test substance at a concentration of $C_q$ $(I_{air})$, and $O_{air}$ represents the emission intensity measured for a solution without test substance. Next, under saturated oxygen conditions, emission intensity was measured for a solution with a test substance at the same concentration $C_q$ ($I_{3O2}$). Using these emission intensities, the correction term $F_{air}$ was obtained in accordance with the following equation.

$$F_{air} = \{1+(1-I_{air}/I_{3O2})\}/(I_{air}/I_{3O2}-0.2)-1$$

Interference attributed to the test substance with respect to the photosensitization reaction system was corrected by multiplying $I_{Oair}/I_{air}$ by $F_{air}$. The thus-corrected ratio was expressed as $(I_{Oai}/I_{air})'$. In this procedure, 5 or more different concentrations were employed so that the ratio $O_{air}/I_{air}$ is within the range between 1 and 8.

Subsequently, by the Stern-Volmer method, the above results were plotted in X-Y coordinates, in which the X-axis represents the concentration of a test substance and the Y-axis represents $(I_{Oai}/I_{air})'$, to obtain a linear correlation.

Using the following equation:

$$(I_{Oai}/I_{ai})' = 1 + k_q \cdot \tau \cdot C_q$$

$k_q$ was obtained from the slope of the resulting straight line ($k_q$: the quenching rate constant of singlet oxygen). The results are shown in Table 1. Here, the life time of singlet oxygen in ethanol represented by $\tau$ in the above equation was taken as 10 μs.

TABLE 1

| Test substance | Extinction rate constant of singlet oxygen $(M^{-1}s^{-1})$ |
|---|---|
| Compound (1) | $2.2 \times 10^8$ |
| Compound (2) | $2.0 \times 10^8$ |
| Compound (3) | $2.3 \times 10^8$ |
| Compound (4) | $2.1 \times 10^8$ |
| Compound (5) | $1.5 \times 10^8$ |
| Compound (6) | $1.1 \times 10^8$ |
| Compound (32) | $1.6 \times 10^8$ |
| Compound (33) | $1.4 \times 10^8$ |
| Compound (34) | $1.7 \times 10^8$ |
| Compound (35) | $2.2 \times 10^8$ |
| Compound (36) | $5.8 \times 10^7$ |

Test Example 3:

Inhibition of erythema formation

The hair of white guinea pigs (8 weeks old, female) hair was removed by shaving, and an ethanol solution containing a test substance (5 wt. %) was applied to the shaved part of each animal. A mixture of UV-A/UV-B (40 J/cm², measured at 365 nm using a UV-radiometer UVR-305/365-D, Torex Co.) was irradiated onto the back of each guinea pig using a solar simulator Model 1600 (Solar Light Co.). After 1 day and 2 days of irradiation, the erythema formation was visually determined by the standards of the Japanese Dermatological Association to obtain erythema inhibition ratios. The results are shown in Table 2.

TABLE 2

| Test substance | Erythema inhibition rate (%) |
|---|---|
| Compound (1) | 68 |
| Compound (2) | 42 |
| Compound (3) | 71 |
| Compound (4) | 69 |
| Compound (5) | 65 |
| Compound (6) | 37 |
| Compound (32) | 53 |
| Compound (33) | 43 |
| Compound (34) | 65 |
| Compound (35) | 78 |
| Compound (36) | 48 |
| Comparative compound (1) (Methyl p-methoxycinnamate) | 31 |

Test Example 4:

Inhibition of sunburn cell formation

Ethanol solution of a test substance (1 wt. %) was applied onto the skin of ICR/HR mice. UV-B (100 mJ/cm²) was irradiated onto the skin (health lamp SE20/SLE, Toshiba). Twenty-four hours later, the skin was biopsied and stained using hematoxylin & eosin, after which the number of sunburn cells were counted under microscope. The results are shown in Table 3.

TABLE 3

| Test substance | Inhibition ratio regarding sunburn cell formation (%) |
|---|---|
| Compound (1) | 79 |
| Compound (2) | 53 |
| Compound (3) | 86 |
| Compound (4) | 81 |
| Compound (5) | 65 |
| Compound (6) | 46 |
| Compound (32) | 61 |
| Compound (33) | 54 |
| Compound (34) | 64 |
| Compound (35) | 81 |
| Compound (36) | 62 |
| Comparative compound (1) (Methyl p-methoxycinnamate) | 37 |
| Comparative compound (2) (Cadmium chloride) | 67 |

Test Example 5:

Inhibition of delayed darkening

The hair of colored guinea pigs (8 week old, female) hair was removed, and an ethanol solution containing a test substance (7 wt. %) was applied to the skin. A mixture of UV- A/UV-B rays (50 J/cm², measured at 365 nm using a UV-radiometer UVR-305/365-D, Torex Co.) was irradiated onto the back of each guinea pig using a solar simulator. Fourteen days after irradiation, delayed darkening inhibition ratios were measured using a color difference meter (Model 1001P. Nippon Kogyo Co., Ltd.). The results are shown in Table 4.

TABLE 4

| Test substance | $\Delta\Delta L$ value |
|---|---|
| Compound (1) | 1.7 |
| Compound (2) | 1.1 |
| Compound (3) | 2.0 |
| Compound (4) | 1.8 |
| Compound (5) | 1.5 |
| Compound (6) | 1.1 |
| Compound (32) | 1.3 |
| Compound (33) | 1.1 |
| Compound (34) | 1.3 |
| Compound (35) | 1.9 |
| Compound (36) | 1.2 |
| Comparative compound (1) (Methyl p-methoxycinnamate) | 0.9 |
| Comparative compound (3) (Hydroquinone) | 0.7 |
| Blank | 0.1 |

Test Example 6:

Inhibition of immediate pigment darkening

An ethanol solution containing a test substance (0.5 wt. %) was added to a mixture of dopa (1 mM) and porphyrin (5 mM). A mixture of UV-A/UV-B (3 J/cm², measured at 365 nm) was irradiated onto the resultant mixture using a solar simulator. The amount of dopachrome formed by irradiation was determined by measuring absorption at 475 nm. The results are shown in Table 5.

TABLE 5

| Test substance | Inhibition ratio regarding immediate blackening (%) |
| --- | --- |
| Compound (1) | 71 |
| Compound (2) | 57 |
| Compound (3) | 83 |
| Compound (4) | 76 |
| Compound (5) | 65 |
| Compound (6) | 53 |
| Compound (32) | 56 |
| Compound (33) | 67 |
| Compound (34) | 63 |
| Compound (35) | 78 |
| Compound (36) | 64 |
| Comparative compound (4) (Sodium azide) | 48 |
| Comparative compound (5) (Ascorbic acid) | 42 |

Test Example 7:

Inhibition of protein denaturation

An ethanol solution containing a test substance (0.1 wt. %) was added to a mixture of collagen (0.5 mg/ml) and 2 porphyrin (100 mM). A mixture of UV-A/UV-B (3 J/cm$^2$, measured at 365 nm) was irradiated onto the resultant mixture using a solar simulator. The irradiated mixture was applied to SDS-PAGE electrophoresis, and collagen crosslinking inhibition ratios were measured. The results are shown in Table 6.

TABLE 6

| Test substance | Protein denaturation inhibition ratio (%) |
| --- | --- |
| Compound (1) | 85 |
| Compound (2) | 62 |
| Compound (3) | 93 |
| Compound (4) | 87 |
| Compound (5) | 81 |
| Compound (6) | 53 |
| Compound (32) | 88 |
| Compound (33) | 44 |
| Compound (34) | 61 |
| Compound (35) | 84 |
| Compound (36) | 69 |
| Comparative compound (4) (Sodium azide) | 45 |
| Comparative compound (6) (α-Tocopherol) | 30 |

Test Example 8:

Inhibition of lipid peroxide formation

Cultured human fibroblasts were combined with 100 mM porphyrin and a test substance (0.01 wt. %, in ethanol). A mixture of UV-A/UV-B rays (1 J/cm$^2$, measurements performed at 365 nm) was irradiated onto the resultant cell culture using a solar simulator. The fibroblasts were collected after the trypsin treatment, then extracted hydrophobic substances using acetone. The extracted substances were dried under nitrogen to prepare cellular lipid samples. A TBA method was used to measure lipid peroxides in cells and inhibition ratio by a test substance. The results are shown in Table 7.

TABLE 7

| Test substance | Inhibition ratio regarding lipid peroxide formation |
| --- | --- |
| Compound (1) | 51 |
| Compound (2) | 43 |
| Compound (3) | 60 |
| Compound (4) | 57 |
| Compound (5) | 48 |
| Compound (6) | 40 |
| Compound (32) | 54 |
| Compound (33) | 47 |
| Compound (34) | 52 |
| Compound (35) | 56 |
| Compound (36) | 46 |
| Comparative compound (4) (Sodium azide) | 37 |
| Comparative compound (5) (Ascorbic acid) | 43 |
| Comparative compound (6) (α-Tocopherol) | 42 |

Test Example 9:
Prevention of DNA damage

To a mixture of 1 g E. coli vector pUC119 DNA and 100 mM porphyrin, an ethanol solution containing a test substance (0.01 wt. %) was added. A mixture of UV-A/UV-B (3 J/cm$^2$, measured at 365 nm) was irradiated onto the resultant DNA mixture using a solar simulator. A 2.5-fold amount of ethanol and a 0.1-fold amount of 5M sodium acetate were added and the DNA was precipitated. The DNA pellet was dissolved in a TE buffer, and analyzed through agarose gel electrophoresis. Inhibition of DNA single strand breaks formation was measured. The results are shown in Table 8.

TABLE 8

| Test substance | Prevention of DNA damage (%) |
| --- | --- |
| Compound (1) | 69 |
| Compound (2) | 50 |
| Compound (3) | 71 |
| Compound (4) | 69 |
| Compound (5) | 66 |
| Compound (6) | 47 |
| Compound (32) | 61 |
| Compound (33) | 48 |
| Compound (34) | 64 |
| Compound (35) | 79 |
| Compound (36) | 58 |
| Comparative compound (4) (Sodium azide) | 53 |
| Comparative compound (5) (Ascorbic acid) | 21 |
| Comparative compound (6) (α-Tocopherol) | 34 |

Test Example 10:
Inhibition of wrinkle formation in the skin of mice

To the back of each ICR/HR mouse (female, 6 weeks old), an ethanol solution containing a test substance (1 wt. %) was applied. One (1) MED of UV-B was irradiated thereto using a health lamp SL20-SLE (Toshiba). Irradiation was repeated five times per week over sixteen weeks. Wrinkle formation was visually scored using the following five rankings.

0: No wrinkles observed
1: Mild and questionable wrinkles are observed
2: Mild but clear and definite wrinkles are observed
3: Moderate wrinkles are observed
4: Severe wrinkles are observed Using the above rankings, wrinkle formations were scored and the inhibition ratios were determined by the division by the blank score. The results are shown in Table 9.

TABLE 9

| Test substance | Inhibition of wrinkle formation (%) |
| --- | --- |
| Compound (1) | 47 |
| Compound (2) | 38 |
| Compound (3) | 58 |
| Compound (4) | 51 |
| Compound (5) | 43 |
| Compound (6) | 36 |
| Compound (32) | 43 |
| Compound (33) | 35 |
| Compound (34) | 43 |
| Compound (35) | 42 |
| Compound (36) | |
| Comparative compound (4) (Sodium azide) | 28 |
| Comparative compound (5) (Ascorbic acid) | 11 |
| Comparative compound (6) (α-Tocopherol) | 34 |

Test Example 11:

(1) Inhibition of wrinkle formation in hairless mice.

To each hairless mouse (HR/ICR, 6 weeks old when the test started), a test substance (5 wt. %, in ethanol) was applied. (80 μl). Approximately 10 minutes later, UV-B was irradiated thereto using 6 bulbs of health lamps (SL20-SLE, Toshiba) so that the dose per irradiation was not greater than 1 MED. Irradiation was repeated five times per week over sixteen weeks. While the irradiation energy was measured using a UV-radiometer (UVR-305/S65D, Tokyo Optical K.K.) so that the dose per irradiation was not greater than 1 MED, energy was irradiated at an intensity of 0.28 mW/cm$^2$, with the total dose. 100 mJ/cm$^2$. As a control, a case where only ethanol was applied was similarly tested in a manner performed on the test substances.

After completion of the testing, the level of wrinkle formation was visually determined using the following standards (wrinkle indices).

Wrinkle indices:

1: No wrinkles are formed

2: Small amounts of wrinkles are formed

3: Moderate amounts of wrinkles are formed

4: Considerable amounts of wrinkles are formed (2) Analysis of wrinkles

In order to analyze the wrinkles formed in the above step (1) in detail, replicas of different skin areas (3 replicas per mouse) each having a round shape with a diameter of 1 cm were obtained using a hydrophilic exaflex, hydrophilic vinyl silicone imaging agent. Each replica was placed horizontally and lightened from an angle of 30°. The area of shadows formed by wrinkles was analyzed as the area ratio using an image analyzing apparatus.

The results are shown in Table 10.

TABLE 10

| Compound | Wrinkle index | Area ratio of image analysis (%) |
| --- | --- | --- |
| Compound (21) | 2.35 ± 0.40 | 3.59 ± 0.44 |
| Compound (22) | 2.34 ± 0.16 | 3.37 ± 0.30 |
| Compound (23) | 2.17 ± 0.05 | 3.23 ± 0.18 |
| Compound (24) | 2.56 ± 0.08 | 3.27 ± 0.29 |
| Compound (25) | 2.35 ± 0.34 | 3.32 ± 0.21 |
| Compound (26) | 2.44 ± 0.33 | 3.69 ± 0.59 |
| Compound (27) | 2.22 ± 0.17 | 3.73 ± 0.29 |
| Compound (28) | 2.43 ± 0.06 | 3.24 ± 0.33 |
| Compound (29) | 2.28 ± 0.06 | 3.64 ± 0.12 |
| Compound (30) | 2.51 ± 0.43 | 3.39 ± 0.47 |
| Compound (31) | 2.49 ± 0.20 | 3.30 ± 0.17 |
| α-Tocopheryl acetate | 3.28 ± 0.23 | 4.67 ± 0.48 |
| Control | 3.78 ± 0.08 | 6.46 ± 0.68 |

Formulation Example 1: W/O cream:

| | |
| --- | --- |
| (1) Compound (6) | 0.01 (wt. %) (2) |
| (2) Cholesterol | 0.5 |
| (3) Cholesterol isostearate | 1.0 |
| (4) Polyether-modified silicone | 1.5 |
| (5) Cyclic silicone | 20.0 |
| (6) Methylphenyl polysiloxane | 2.0 |
| (7) Methyl polysiloxane | 2.0 |
| (8) Magnesium sulfate | 0.5 |
| (9) 55% Ethanol | 5.0 |
| (10) Carboxymethyl chitin (Chitin Liquid HV, product of Ichimaru Pharcos) | 0.5 |
| (11) Purified water | balance |

Ingredients (1) through (7) were heated and dissolved at 80° C. To the resultant solution, ingredients (8) through (11) were added and uniformly mixed to prepare a W/O cream.

Formulation Example 2: O/W cream:

| | |
| --- | --- |
| (1) Polyoxyethylene (10) hydrogenated castor oil | 1.0 (wt. %) |
| (2) Sorbitan monostearate | 0.5 |
| (3) Sodium stearoyl methyltaurate | 0.5 |
| (4) Cetostearyl alcohol | 2.0 |
| (5) Stearic acid | 1.8 |
| (6) Compound (5) | 0.1 |
| (7) Cholesterol | 1.5 |
| (8) Cholesterol isostearate | 1.0 |
| (9) Neopentylglycol dicaprylate | 8.0 |
| (10) Methyl polysiloxane | 5.0 |
| (11) Glycerol | 5.0 |
| (12) Purified water | balance |

Ingredients (1) through (10) were dissolved at 80° C. To the resultant solution, ingredients (11) and (12) were added and uniformly mixed to prepare an O/W cream.

Formulation Example 3: Moisturizing sunscreen cream:

| | |
| --- | --- |
| (1) Compound (3) | 0.2 (wt. %) |
| (2) Silicone-coated $ZnO_2$ | 7.0 |
| (3) 2-Ethylhexyl p-methoxycinnamate | 3.0 |
| (4) Cholesteryl isostearate | 1.0 |
| (5) Polyether-modified silicone | 2.0 |
| (6) Methyl polysiloxane | 5.0 |
| (7) Cyclic silicone | 15.0 |
| (8) Magnesium sulfate | 1.0 |
| (9) Glycerol | 5.0 |
| (10) Purified water | balance |

Ingredients (1) through (7) were heated and dissolved at 80° C. To the resultant solution, ingredients (8) through (10) were added and uniformly mixed to prepare a moisturizing sunscreen cream.

| Formulation Example 4: Ointment: | |
|---|---|
| (1) Compound (1) | 0.1 (wt. %) |
| (2) White Vaseline | balance |
| (3) Cholesteryl isostearate | 3.0 |
| (4) Liquid paraffin | 10.0 |
| (5) Glyceryl ether | 1.0 |
| (6) Glycerol | 10.0 |

Ingredients (1) through (6) were heated and dissolved at 80° C. The resultant solution was cooled to prepare an ointment.

| Formulation Example 5: Pack: | |
|---|---|
| (1) Compound (2) | 1.0 (wt. %) |
| (2) Polyvinyl alcohol | 15.0 |
| (3) Carboxymethylcellulose Na | 5.0 |
| (4) Propylene glycol | 3.0 |
| (5) Ethanol | 8.0 |
| (6) Purified water | balance |
| (7) Perfume | 0.5 |
| (8) Preservative, antioxidant | suitable amounts |

Ingredients (1) through (8) were heated and dissolved at 70° C. The resultant solution was cooled to prepare a pack composition.

| Formulation Example 6: Lotion: | |
|---|---|
| (1) 1,3-Butylene glycol | 8.0 (wt. %) |
| (2) Glycerol | 4.0 |
| (3) Sodium hyaluronate | 1.0 |
| (4) Ethanol | 3.0 |
| (5) Polyoxyethylene polyoxypropylene decyltetradecyl ether | 0.3 |
| (6) Compound (4) | 0.1 |
| (7) Purified water | balance |
| (8) Preservative | suitable amount |

| Formulation Example 7: Creamy hair conditioner: | |
|---|---|
| (1) Compound (7) | 0.2 (wt. %) |
| (2) Cetostearyltrimethylammonium chloride | 2.0 |
| (3) Silicone KF6002 (Polyether-modified silicone, Shin-Etsu Chemical Co., Ltd.) | 3.0 |
| (4) 2-Ethylhexyl 4-methoxycinnamate | 0.2 |
| (5) Cetanol | 2.0 |
| (6) Butylhydroxytoluene | 0.1 |
| (7) Kason CG | 3 ppm |
| (8) Hydroxyethylcellulose | 0.5 |
| (9) Colorant (Green #3) | trace amount |
| (10) Purified water | balance |
| (11) Perfume | 0.5 |

Ingredients (1) through (11) were processed using a standard procedure to prepare a creamy hair conditioner.

| Formulation Example 8: Hair styling foam: | |
|---|---|
| (1) Compound (5) | 2.0 (wt. %) |
| (2) Dimethylpolysiloxane (10,000 cs) | 3.0 |
| (3) Octamethylcyclotetrasiloxane | 10.0 |
| (4) Glycerol | 2.0 |
| (5) Emanone CH80 (Nonionic surfactant, Kao Corp.) | 2.0 |
| (6) Ethanol | 15.0 |
| (7) Perfume | 0.2 |
| (6) n-Butane | 7.0 |
| (9) Purified water | balance |

Ingredients (1) through (9) were processed using a standard procedure to prepare a hair styling foam.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound represented by the following formula (1c) or a salt thereof:

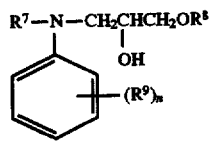

(1c)

wherein $R^7$ represents an alkyl group, $R^8$ represents a hydrogen atom or an alkyl group; each R9, in the number of n, independently represents a hydrogen atom, an alkyl group, or an alkoxyl group; and n represents an integer of from 1 to 4; with the proviso that when: (1) $R^8$ and $R^9$s in the number of n are all hydrogen atoms; (2) $R^8$ is a hydrogen atom, $R^7$ is an ethyl group, n is 1, and $R^9$ is a methyl group substituted at the meta-position; (3) $R^7$ and $R^8$ are both methyl groups and $R^9$s in the number of n are all hydrogen atoms; or (4) $R^7$ and $R^8$ are both methyl groups, n is 1, and $R^9$ is a methyl group substituted at the meta-position, the resulting compounds are excluded.

2. The compound according to claim 1 or a salt thereof, wherein $R^7$ represents a C1–C12 alkyl group; $R^8$ represents a hydrogen atom or a C1–C12 alkyl group; each $R^9$, in the number of n, independently represents a hydrogen atom, a C1–C12 alkyl group, or a C1–C10 alkoxyl group; and n represents an integer of from 1 to 4; with the proviso that when: (1) $R^8$ and $R^9$s in the number of n are all hydrogen atoms; (2) $R^8$ is a hydrogen atom, $R^7$ is an ethyl group, n is 1, and $R^9$ is a methyl group substituted at the meta-position; (3) $R^7$ and $R^8$ are both methyl groups and $R^9$s in the number of n are all hydrogen atoms; or (4) $R^7$ and $R^8$ are both methyl groups, n is 1, and $R^9$ is a methyl group substituted at the meta-position, the resulting compounds are excluded.

3. A singlet oxygen quencher composition, comprising, as an active singlet oxygen quenching component, an N,N-disubstituted aniline compound represented by the following formula (1c) or a salt thereof.

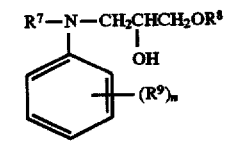

(1c)

wherein $R^7$ represents an alkyl group, $R^8$ represents a hydrogen atom or an alkyl group; each $R^9$, in the number of n, independently represents a hydrogen atom, an alkyl group, or an alkoxyl group; and n represents an integer of from 1 to 4; with the proviso that when: (1) $R^8$ and $R^9$s in the number of n are all hydrogen atoms; (2) $R^8$ is a hydrogen atom, $R^7$ is an ethyl group, n is 1, and $R^9$ is a methyl group substituted at the meta-position; (3) $R^7$ and $R^8$ are both methyl groups and $R^9$s in the number of n are all hydrogen atoms; or (4) $R^7$ and $R^8$ are both methyl groups, n is 1, and $R^9$ is a methyl group substituted at the meta-position, the resulting compounds are excluded;

in a suitable carrier.

4. An external composition comprising an effective singlet oxygen quenching amount of an N,N-disubstituted aniline compound represented by the following formula (1c) or a salt thereof:

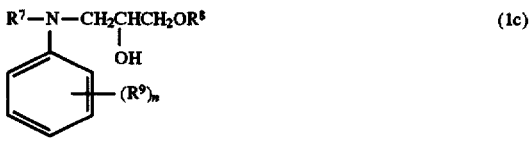

(1c)

wherein $R^7$ represents an alkyl group, $R^8$ represents a hydrogen atom or an alkyl group; each $R^9$, in the number of n, independently represents a hydrogen atom, an alkyl group, or an alkoxyl group; and n represents an integer of from 1 to 4; with the proviso that when: (1) $R^8$ and $R^9$s in the number of n are all hydrogen atoms; (2) $R^8$ is a hydrogen atom, $R^7$ is an ethyl group, n is 1, and $R^9$ is a methyl group substituted at the meta-position; (3) $R^7$ and $R^8$ are both methyl groups and $R^9$s in the number of n are all hydrogen atoms; or (4) $R^7$ and $R^8$ are both methyl groups, n is 1, and $R^9$ is a methyl group substituted at the meta-position, the resulting compounds are excluded;

in a dermatologically acceptable carrier.

5. A method for the treatment or prevention of skin or hair damage due to singlet oxygen, comprising:

applying, to a subject in need thereof, a composition as claimed in claim 3.

* * * * *

UNITED STATES PATENT AND TRADEMARK OFFICE
CERTIFICATE OF CORRECTION

PATENT NO. : 5,709,816
DATED : January 20, 1998
INVENTOR(S) : Masakazu YAMAGUCHI et al.

It is certified that error appears in the above-indentified patent and that said Letters Patent is hereby corrected as shown below:

On the title page, Item [30], the first Foreign Application date should read:

-- Jul. 21, 1995 --

Signed and Sealed this

Thirty-first Day of March, 1998

Attest:

BRUCE LEHMAN

Attesting Officer        Commissioner of Patents and Trademarks